US007555492B2

(12) United States Patent
Herzenberg et al.

(10) Patent No.: US 7,555,492 B2
(45) Date of Patent: Jun. 30, 2009

(54) SYSTEM AND METHOD FOR INTERNET-ACCESSIBLE TOOLS AND KNOWLEDGE BASE FOR PROTOCOL DESIGN, METADATA CAPTURE AND LABORATORY EXPERIMENT MANAGEMENT

(75) Inventors: Leonore Herzenberg, Stanford, CA (US); Stephen Meehan, Vancouver (CA); Wayne Moore, San Francisco, CA (US); David Parks, San Francisco, CA (US); James Tung, Menlo Park, CA (US); Mark Musen, Stanford, CA (US)

(73) Assignee: The Board of Trustees at the Leland Stanford Junior University, Palo Alto, CA (US)

( * ) Notice: Subject to any disclaimer, the term of this patent is extended or adjusted under 35 U.S.C. 154(b) by 417 days.

(21) Appl. No.: 10/833,164

(22) Filed: Apr. 26, 2004

(65) Prior Publication Data

US 2005/0044110 A1 Feb. 24, 2005

Related U.S. Application Data

(63) Continuation-in-part of application No. 09/860,222, filed on May 18, 2001, now Pat. No. 6,947,953, and a continuation-in-part of application No. 09/434,240, filed on Nov. 5, 1999, now abandoned.

(60) Provisional application No. 60/526,509, filed on Dec. 2, 2003, provisional application No. 60/465,840, filed on Apr. 24, 2003, provisional application No. 60/205,489, filed on May 19, 2000.

(51) Int. Cl.
 *G06F 17/30* (2006.01)
(52) U.S. Cl. .................................. 707/102; 707/104.1

(58) Field of Classification Search ............... 707/1–10, 707/100–104.1, 200, 201, 203–205; 700/90, 700/266; 702/1, 19, 22; 705/1–4, 26–29; 706/10, 15, 16, 23, 25, 45, 903, 906; 709/200–203, 709/217–219; 128/920; 600/300
See application file for complete search history.

(56) References Cited

U.S. PATENT DOCUMENTS 5,379,422 A * 1/1995 Antoshenkov ................. 707/1

(Continued)

FOREIGN PATENT DOCUMENTS

WO PCT/US01/16375 6/2004

OTHER PUBLICATIONS

MA Musen and A. Th. Schreiber. "Architectures for intelligent systems based on reusable components", 1995, Artificial Intelligence in Medicine, 7, pp. 189-199.*

(Continued)

*Primary Examiner*—Debbie M Le
(74) *Attorney, Agent, or Firm*—Greenberg Traurig, LLP

(57) ABSTRACT

The present invention is related to databases and the exchange of scientific information. Specifically the invention discloses a laboratory data management system including a knowledge base that stores characteristics of laboratory reagents, experiment subjects, tissues and cells. The invention also includes an experiment input module that accepts input of parameters of an experiment and data from a knowledge base module. Further, the invention includes a protocol creator connected to the knowledge base module and the experiment input module that creates a laboratory protocol for an experiment based on data supplied from the knowledge base module and the experiment input module. The invention also includes methods to use the described system.

68 Claims, 36 Drawing Sheets

U.S. PATENT DOCUMENTS

| | | | | |
|---|---|---|---|---|
| 6,003,039 | A * | 12/1999 | Barry et al. | 707/103 R |
| 6,108,635 | A * | 8/2000 | Herren et al. | 705/2 |
| 6,185,561 | B1 * | 2/2001 | Balaban et al. | 707/6 |
| 6,261,229 | B1 * | 7/2001 | Gotschim et al. | 600/300 |
| 6,408,308 | B1 * | 6/2002 | Maslyn et al. | 707/104.1 |
| 6,675,166 | B2 * | 1/2004 | Bova | 707/10 |
| 6,772,160 | B2 * | 8/2004 | Cho et al. | 707/10 |
| 6,850,252 | B1 * | 2/2005 | Hoffberg | 715/716 |
| 2001/0032210 | A1 * | 10/2001 | Frank et al. | 707/104.1 |
| 2001/0039014 | A1 * | 11/2001 | Bass et al. | 702/20 |
| 2001/0044134 | A1 * | 11/2001 | Sheppard | 435/6 |
| 2002/0012905 | A1 * | 1/2002 | Snodgrass | 702/19 |
| 2002/0059326 | A1 * | 5/2002 | Bernhart et al. | 707/203 |
| 2002/0083034 | A1 * | 6/2002 | Orbanes et al. | 707/1 |
| 2002/0177138 | A1 * | 11/2002 | Boissy | 702/20 |
| 2002/0194154 | A1 * | 12/2002 | Levy et al. | 707/1 |
| 2004/0172382 | A1 * | 9/2004 | Prang et al. | 707/2 |
| 2004/0259111 | A1 * | 12/2004 | Marlowe et al. | 435/6 |
| 2006/0045348 | A1 * | 3/2006 | Kiros et al. | 382/190 |
| 2006/0047697 | A1 * | 3/2006 | Conway et al. | 707/103 R |

OTHER PUBLICATIONS

Ben-Basat M., et al.: "A Hierarchical Modular Design for Treatment Protocols" Dialog Embase, 1980, XP002913397.

Gordon Good: "The LDAP data Interchange Format (LDIF)—Technical Specification <draft-good-Idap-Idif-05.tex>" IDTF DRAFT, 'online! Oct. 19, 1999, pp. 1-16, XP002267329.

* cited by examiner

SYSTEM AND METHOD FOR INTERNET-ACCESSIBLE TOOLS AND KNOWLEDGE BASE FOR PROTOCOL DESIGN, METADATA CAPTURE AND LABORATORY EXPERIMENT MANAGEMENT

CROSS-REFERENCE TO RELATED APPLICATIONS

This application claims priority to and incorporates in full:

U.S. Provisional Patent Application No. 60/526,509 titled AN INTERNET-LINKED SYSTEM FOR DIRECTORY BASED DATA STORAGE, RETRIEVAL AND ANALYSIS, filed Dec. 2, 2003; and U.S. Provision Patent Application No. 60/465,840 titled AN INTERNET-LINKED SYSTEM FOR DIRECTORY PROTOCOL BASED DATA STORAGE, RETRIEVAL AND ANALYSIS, filed Apr. 24, 2003.

This application is a Continuation-In Part of and incorporates in full U.S. patent application Ser. No. 09/860,222 titled AN INTERNET-LINKED SYSTEM FOR DIRECTORY PROTOCOL BASED DATA STORAGE, RETRIEVAL AND ANALYSIS, filed May 18, 2001, now U.S. Pat. No. 6,947,953, which claims the benefit of U.S. Provisional Application No. 60/205,489 filed May 19, 2000 and is a Continuation-In-Part of U.S. patent application Ser. No. 09/434,240, filed Nov. 5, 1999 now abandoned.

BACKGROUND

I. Fluorescent Activated Cell Sorting (FACS)

Flow cytometry is a technique for obtaining information about cells and cellular processes by allowing a thin stream of a single cell suspension to "flow" through one or more laser beams and measuring the resulting light scatter and emitted fluorescence. Since there are many useful ways of rendering cells fluorescent, it is a widely applicable technique and is very important in basic and clinical science, especially immunology. Its importance is increased by the fact that it is also possible to sort fluorescent labeled live cells for functional studies with an instrument called the Fluorescence Activated Cell Sorter (FACS).

Flow cytometry is computerized because without computers the data analysis would be infeasible. As flow cytometry has matured, the importance of combining flow data with data from other sources has become clear, as has the need for multi site collaborations, particularly for clinical research. This lead to our interest in developing methods for naming or identifying flow cytometry samples, reagents and instruments (among other things) and in maintaining a shared repository of information about the samples etc.

Flow cytometry was revolutionized in the late 1970s with the introduction of monoclonal antibodies that could be coupled to a fluorochrome and used as FACS reagents. However, nomenclature for these reagents has been a hodgepodge, in spite of the fact that monoclonals are useful precisely because they can be uniquely and accurately named, i.e., the antibody produced by a clone is always the same whereas naturally produced sera are highly variable. Our work in capturing the experimental semantics of FACS experiments made it clear that we needed at least a local nomenclature and underscored the value of a global nomenclature for FACS data and monoclonal antibodies, which are useful in many fields beside flow cytometry.

II. DNA Arrays/Microarrays

During the past decade, the development of array-based hybridization technology has received great attention. This high throughput method, in which hundreds to thousands of polynucleotide probes immobilized on a solid surface are hybridized to target nucleic acids to gain sequence and function information, has brought economical incentives to many applications. See, e.g., McKenzie, et al., *Eur. J of Hum. Genet.* 6:417-429 (1998), Green et al., *Curr.Opin. in Chem. Biol.* 2:404-410 (1998), and Gerhold et al., *TIBS*, 24:168-173 (1999).

III. Gels

Gel electrophoresis is a standard technique used in biology. It is designed to allow sample to be pulled through a semisolid medium such as agar by an electromagnetic force. This technique allows for separation of small and macromolecules by either their size or charge.

IV. Prior Art

Although there are wide variety of tools that purport to help scientists deal with the complex data collected in today's laboratories, virtually all of these so-called Laboratory Information Systems (LIMS) or Electronic Laboratory Notebook systems (ELNs) approach data collection and management from the perspective of final data output and interpretation. None of these systems addresses the basic needs of the bench scientist, who lacks even minimal tools for automating the collection and storage of data annotated with sufficient information to enable its analysis and interpretation as a study proceeds.

The absence of automated support for this basic laboratory function, particularly when data is collected with today's complex data-intensive instrumentation, constitutes a significant block to creative and cost-effective research. Except in very rare instances, the study and experiment descriptions that scientists use to interpret the digitized data these instruments generate are stored in paper-bound notebooks or unstructured computer files whose connection to the data must be manually established and maintained. The volatility of these connections, aggravated by turnover in laboratory personnel, makes it necessary to complete the interpretation of digitized data as rapidly as possible and seriously shortens the useful lifetime of data that could otherwise be mined repeatedly.

In addition, because paper notebook or unstructured computer information is difficult to make available to other investigators, particularly at different sites or across time, laboratories that would like to make their primary data or their specific findings available to collaborators or other interested parties are unable to do so. Thus, although computer use now facilitates many aspects of research, and although the Internet now makes data sharing and cooperative research possible, researchers are prevented from taking full advantage of these tools by the lack of appropriately tailored computer support for integrating and accessing their work.

Finally, because the minimal computerized support for research that currently exists has developed piecemeal, usually in response to needs encountered during collection of particular kinds of data, no support currently exists for providing lateral support to integrate different types of data collected within an overall study. For example, although automated methods for collecting, maintaining and using DNA microarray data are now becoming quite sophisticated, the integration of these data with information about the source of the material analyzed, or with data or results from FACS or other types analyses done with the same material, is largely a manual task requiring recovery of data and information stored on paper or in diverse files at diverse locations that are often known only to one or a small number of researchers directly concerned with the details of the project. In fact, it is common for individual bench scientists to repeat experiments sometimes several times because key information or data was "misplaced" or its location lost over time.

V. Protégé

Protégé is a knowledge based programming language developed at Stanford University. Information regarding protégé may be retrieved from the web-site http://protege.stanford.edu. Protégé is an ontology editor and a knowledge-based editor. An ontology is an object oriented database which captures knowledge of a domain. Protégé is also a Java tool that provides an extensible architecture for the creation of customized knowledge-based tools. The tools of Protégé also provide for customized knowledge acquisition forms and the entry of domain knowledge. Protégé further provides a platform that can be extended with graphical widgets for tables, diagrams, and animation components to access other knowledge-based systems embedded application. Last Protégé is a library that other applications can use to access and display knowledge bases.

SUMMARY OF THE INVENTION

The present invention is related to databases and the exchange of scientific information. Specifically the invention includes a laboratory data management system including a knowledge base that stores characteristics of laboratory reagents, experiment subjects, tissues and cells. The invention also includes an experimental input module that accepts input of parameters of an experiment and data from a knowledge base module. Further, the invention includes a protocol creator connected to the knowledge base module and the experiment input module that creates a laboratory protocol for an experiment based on data supplied from the knowledge base module and the experiment input module. The invention also includes other modules that in some embodiments help to implement the methods used with the system.

The invention allows a scientist to interface with a knowledge base to create an experimental protocol. The knowledge base can query an inventory module to allow the system to inform the scientist of what protocols are feasible. The system may also provide information about what other protocols are feasible or what instruments or reagents may be feasibly added to the experimental protocol.

The invention also includes a unified scientific database that allows researchers to easily share their data with other researchers. The present invention also allows for the ease of data collection, annotation, storage, management, retrieval and analysis of scientific data through and into the database. In addition, it allows for storage and retrieval of data collected directly from laboratory instruments to ensure data consistency. It further allows for ease of sharing data between laboratories in remote locations. The present invention also supports the automated creation of experimental protocols and through the capture of the metadata to archive, retrieve and use stored data. The metadata captured in this way is used to provide access to the stored data by enabling identification of data components for data processing and visualization. Archive and data storage components of the present invention may be maintained separately or together but are linked by naming conventions that can specify where the data may be located in the archive or the data store. The naming conventions in the present invention also enable migration the system from one storage medium to another. Data can be stored in original formats dictated by the instrument manufacturers. Metadata can be stored in XML or other conventional formats and written to files stored in the data store.

BRIEF DESCRIPTION OF THE DRAWINGS

FIG. 11 is a display of generated protocol alternatives.

FIG. 12 presents the user with a display of the wells in a plate and the contents of those wells.

FIG. 13 presents the user with a tree structure display of the wells in a plate and the contents of those wells.

FIG. 14 presents the user with a sample window of reagents.

FIG. 16 a window that provides information regarding specific molecular pairs and other reagents.

Figure 1:
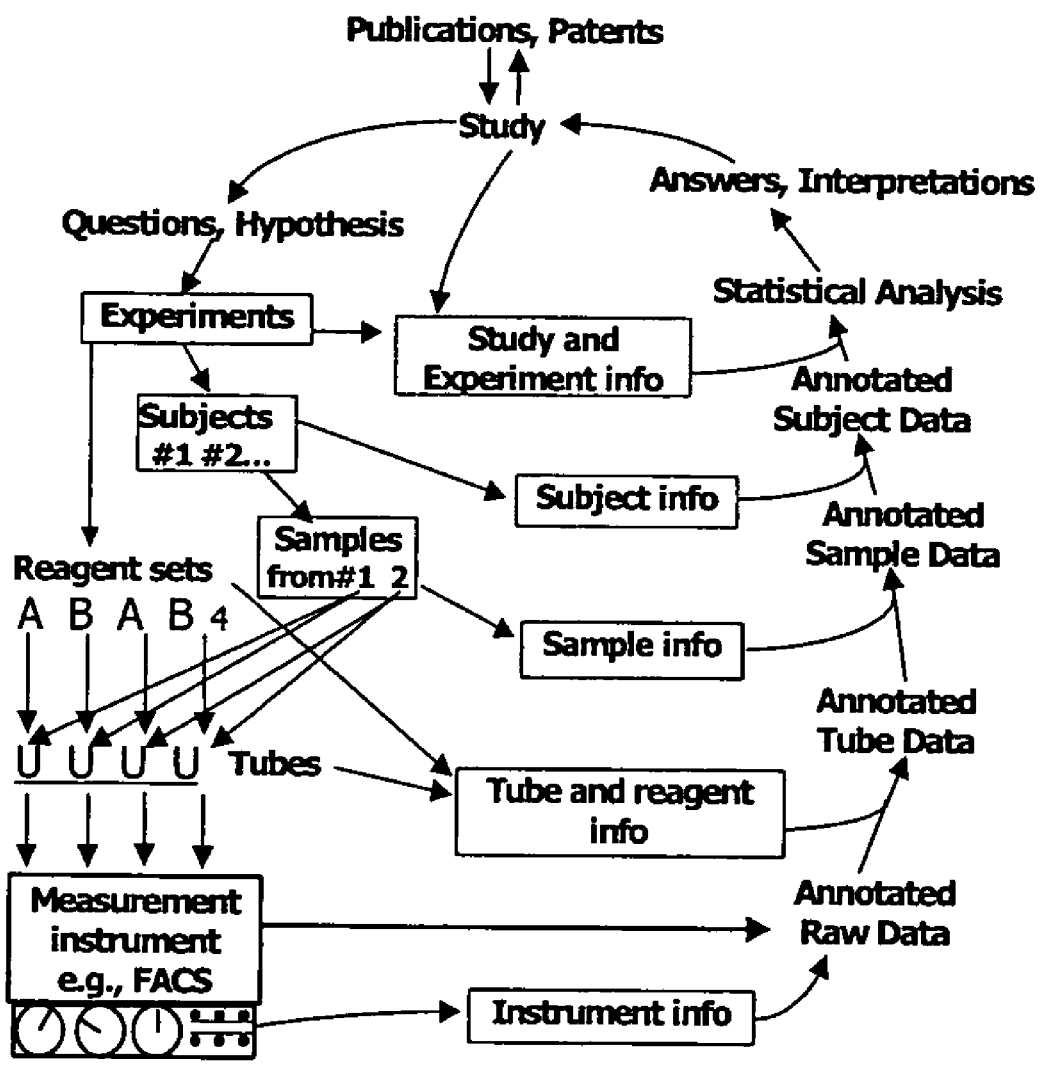
FIG. 1 is a diagram of the flow of information in a biological experiment

FIGS. and SUBFIGS. 19-26 show an embodiment of a system and method of experimental protocol creation.

DETAILED DESCRIPTION

The present invention will be best understood from the point of view of a laboratory worker using the invention. The invention allows the user to simplify laboratory work by allowing interactive automation of much of the work with the use of a computer. The work performed by the present invention makes the researcher more efficient. The steps of the laboratory process the invention addresses includes collecting, sharing, retrieving, analyzing, and annotating data. Although the present invention has equal application to the storage of any data type, one embodiment relates to the storage of data associated with a biological sample data. One embodiment of the present invention includes a knowledge based system designed with the Protégé.

System

In one embodiment the system is configured with several computer systems. The computer systems executed a graphical user interface (GUI) to allow a user to interact with the system. The computer systems also execute a protocol maker module, an experimental input modules and a knowledge base module. These modules, typically software, may also be implemented with hardware. The protocol maker uses information from the knowledge base to create protocols based on inputs from the graphical user interface that in one embodiment includes the experimental input module. The system also provides a mechanism to allow users or others to update scientific and other data in the knowledge base.

In some embodiments other modules are included in and connected to the system. The modules may also be submodules of other modules of the system. First, a laboratory inventory module has capabilities including tracking the stock of reagents in a laboratory. Another module, the laboratory data storage module, has capabilities including the storage of experimental data. Further, an experiment analysis module is able to import experimental data and provide analysis on that experimental data such as automatically creating clusters of cells based on surface markings. The experimental analysis module may also access remote analysis programs to analyze imported experimental data.

Another embodiment uses an updating module to determine if the knowledge base is to be updated with new information and if so, performs an update on the knowledge base. A scheduling module is also implementable to schedule times for researchers to use equipment to conduct their experiments. The module prompts the user with available times for use of the experimental equipment over the GUI and store a selected time in a database in order to reserve the time for the user. An instrument control module provides instructions to experimental equipment to help the user conduct an experiment. For instance, the instructions include information from a protocol on the order in which tubes are to be read by a FACS machine as well as the compensations that are to be performed to calibrate the FACS machine. In another embodiment the system includes a check-in module that coordinates the storage or experiments and protocol information on a laboratory data storage module or a database. The check-in module implements a reformatting tool to store the data in a standard format. A hypothesis testing module may also be implemented automatically determine if a set of data confirms, agrees with or refutes a hypothesis.

The system also connects to scientific and other instrumentation including microarrays and FACS machines. The system and method include the ability to change data formats to be able to communicate with the instrumentation. One method of creating standardized data formats is to use XML and/or metadata.

Figure 3:
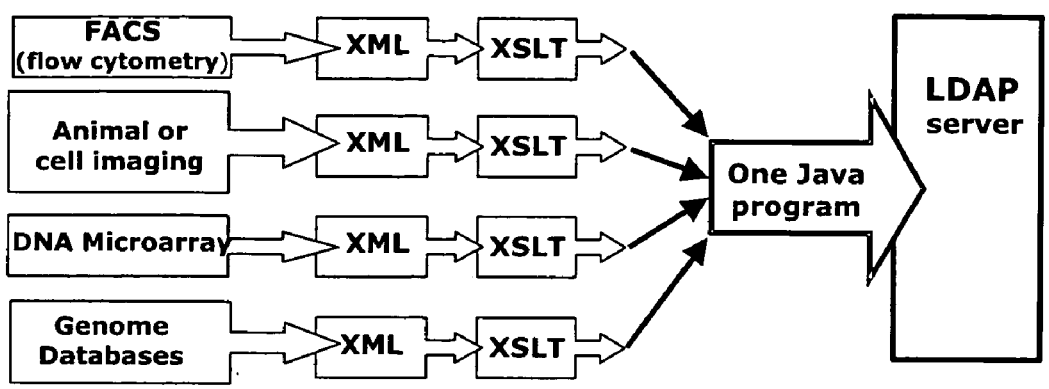
FIG. 3 is a diagram of information flow from instruments to and from the database (IBRSS) in one embodiment of the present invention
Figure 4:
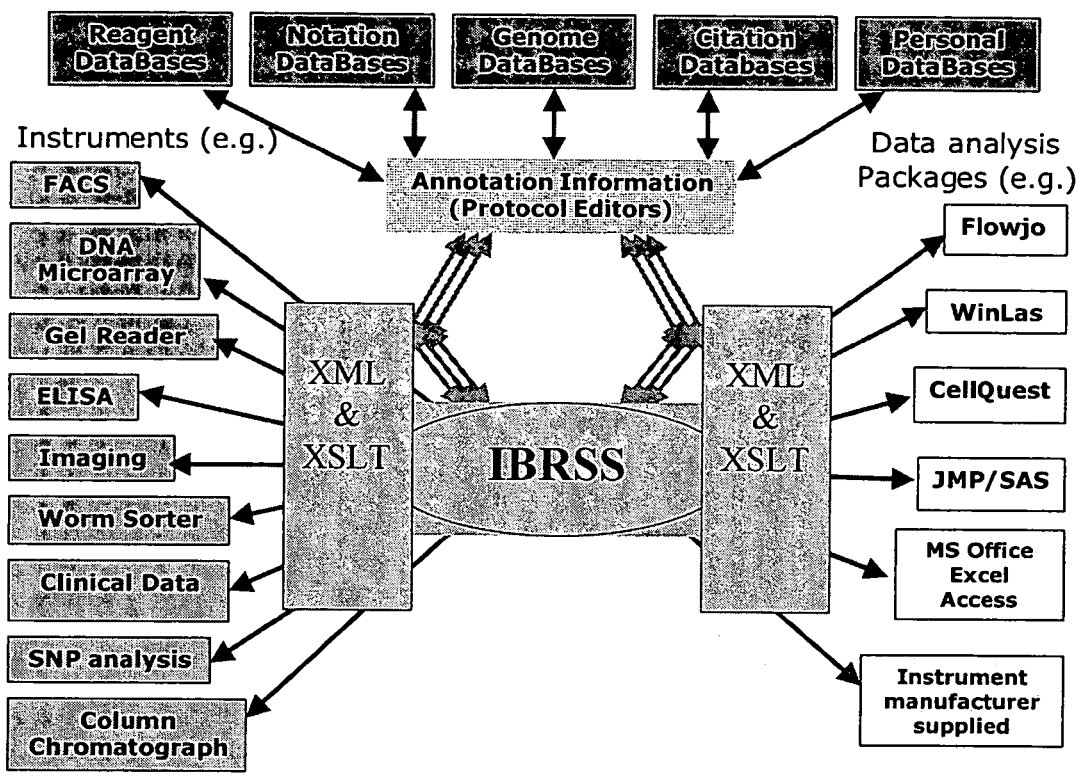
FIG. 4 is a diagram of information flow from instruments, analysis programs, remote databases, and other software and to and from a central database in one embodiment of the present invention.

FIGS. 3 and 4 show two embodiments of at least portions of the system of the present invention. The invention may use other embodiments including those on a single computer or multiple computers. The multiple computers may be on a local area network or connected over the Internet. FIG. 1 describes an exemplary experiment hierarchy and flow that is implementable with the current system and method.

Data Hierarchy

Figure 5A:
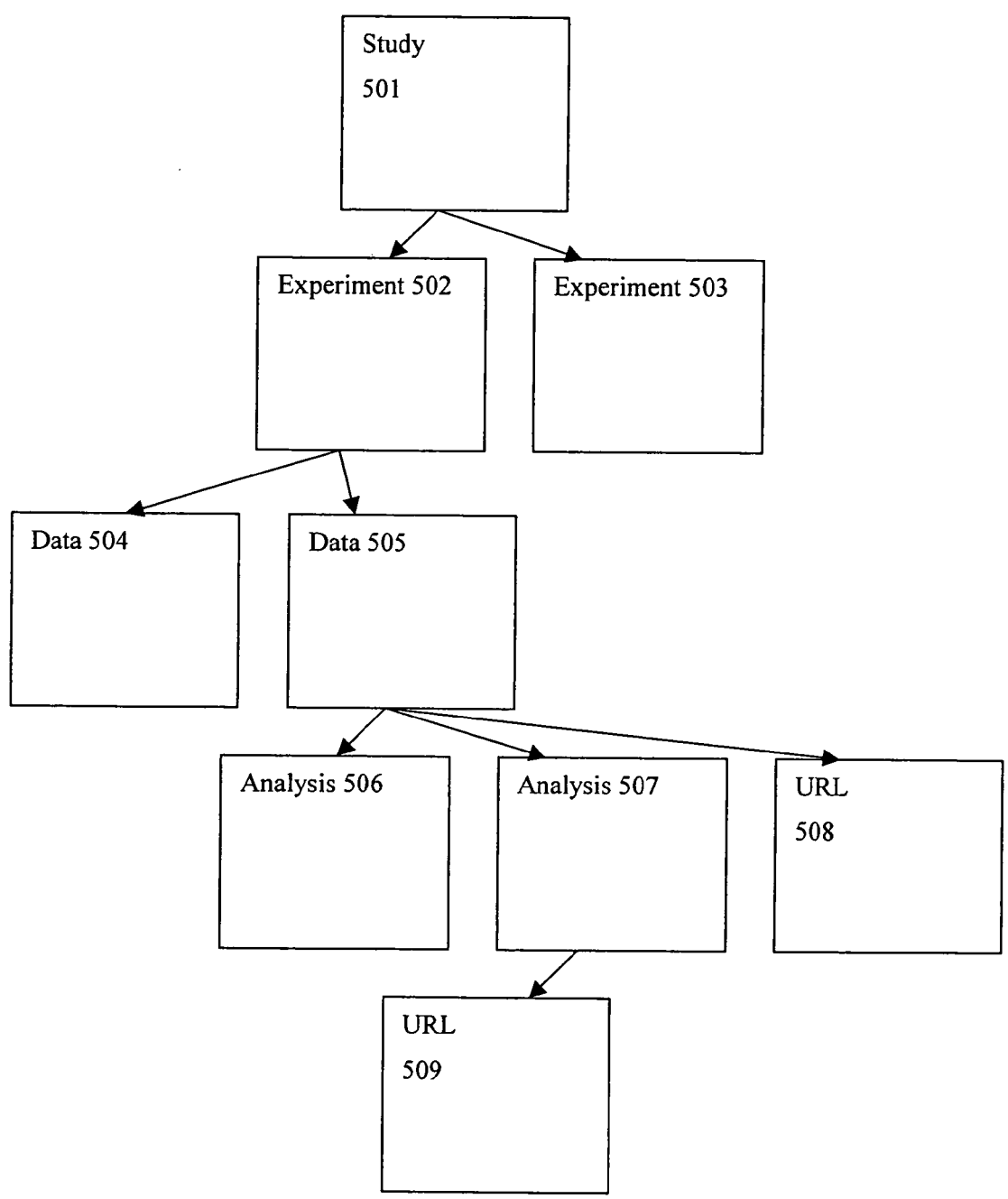
FIG. 5a is a the hierarchical structure of a single study

The data hierarchy may be in the form of a tree. Two possible hierarchies are disclosed in FIGS. 5a and 5b. Hierarchies can be formed in many other ways as well. The first step the researcher performs is to define a study 501. A study is the overall goal of the research the researcher wishes to attain. In the normal course of science a researcher creates experiments to perform the research in the study. The study includes protocols that capture the hypothesis to be tested and the factors that go into them, including subjects, treatments, experiments, samples and the study timeline. In addition, the study may include data and information collected in experiments that are part of the study. This information maybe deposited into the ontology mechanism of the present invention. This information may also be stored in a database or a database accessed through the Protégé ontology.

The present invention allows a researcher to create experiments and experimental protocols 502 and 503 that become part of the overall study. The experiment includes protocols that acquire information to define the subset of subjects for which the data is be collected, the set of samples to be obtained from the subjects, and the analytic procedures and data collection instruments used to analyze the samples. The experiment protocol becomes a child node of its parent study. The data from the experiment may be stored into an archive from which data is stored and retrieved. This data also may be accessed through the Protégé Ontology.

As a typical researcher does today, the researcher using the present invention also obtains data 504 and 505 for each study and experiment he performs. The data may be collected each time the researcher performs the same experiment protocol. The data also include protocols designed to acquire annotation information to define the subdivision (aliquotting) and the treatment (reagents and conditions) for a set of samples for which data may be collected by a single analytical method (usually a single instrument). Researchers then analyze data they obtain, and the researcher using the present invention can analyze the collected data. The data and the analysis again may be stored in a Protégé ontology.

Figure 5B:
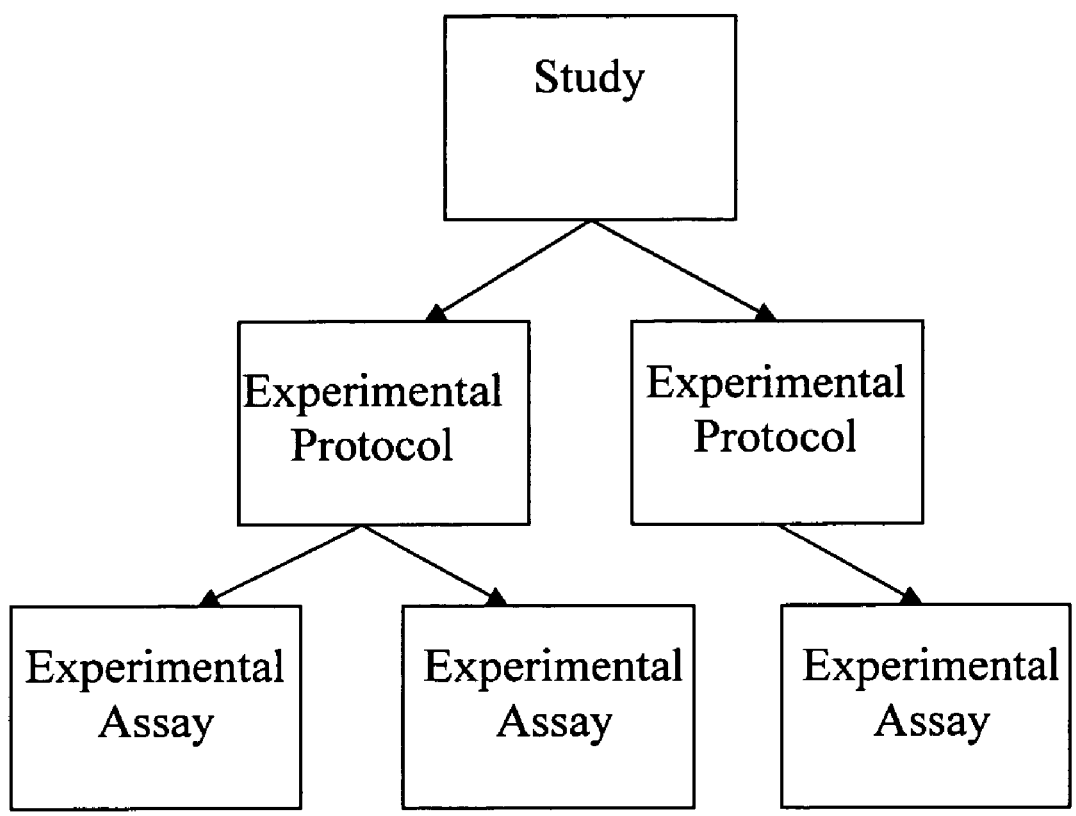
FIG. 5b is a second hierarchical structure of a single study

The organization of data in the present invention may also be in the form of a second tree like hierarchy as described in FIG. 5b. This hierarchy is a study that is comprised of experimental protocols. The experimental protocols is comprised of assay protocols. Regardless of the type of data hierarchy used the data is stored in a Protégé ontology or a database.

When the analysis is complete, the present invention creates Internet addresses for all of the results of the individual analyses and for the data sets created. The present invention may also create hyperlinks or other methods to retrieve the data from a database. These methods of retrieving the data may be stored with the Protégé Ontology. This storage mechanism may also be child nodes 508 and 509 of the data or experiment information. Thus, the present invention allows the user to possess unique web addresses or data access methods for any of the data or analysis results that he may wish to include in a publication. The study, experimental protocol, data collection, and analysis results, may therefore be stored as described in FIG. 5a or FIG. 5b. Also a hyperlink as well as other methods of data retrieval may be stored or associated with the data collection.

Protocol Creation

The study and the experiment are still the touchstone of research science. The present invention allows the researcher to interactively create protocols for studies and experiments. The protocol creator uses interactive windows to ease the researcher's creation of the protocols. The researcher invokes a protocol creator/editor on a computer. The computer provides the researcher with a list of possible studies or experiments the researcher wishes to perform. The computer also provides the ability for the researcher to create an entirely new type of study or experiment. After the type of study or experiment is chosen, the researcher then may be a given the option of how to set up the experiment.

Several types of possible studies, experiments and options are listed here, however other types of structures for data may be used with the present invention. The types of experiments that will be described in this application specifically are clinical and basic studies and FACS and electrophoresis gel experiments. Other types of data that can be similarly stored and used within the database include DNA microarray data and clinical data. The clinical data includes red blood cell counts and RBC, MCV, MHC, MCHC, and potassium levels or includes observational data such as blood pressure, temperature, types of drugs taken, race, age, etc.

Figure 6:
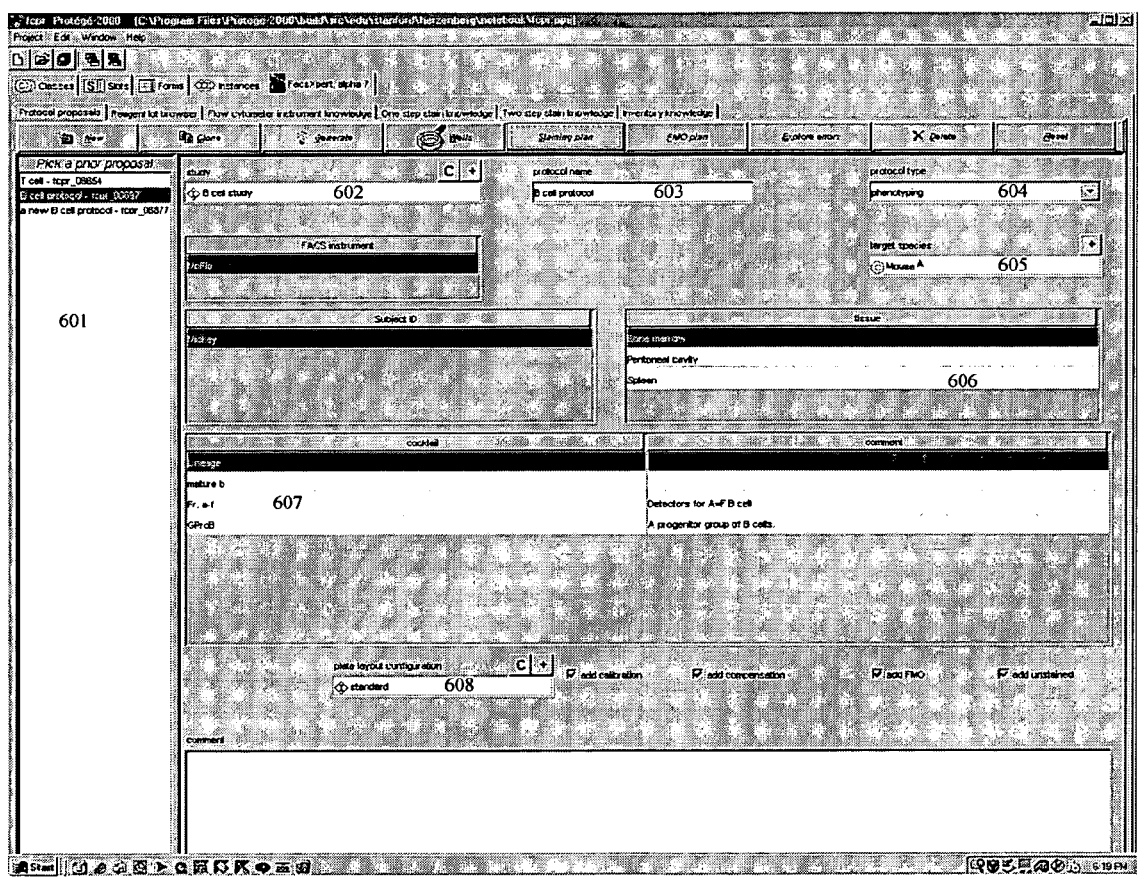
FIG. 6 is a basic display of a protocol selection

FIG. 6 demonstrates a screen that allows for the selection of a protocol. This may be the beginning of the process by which a researcher creates a protocol with the aid of the present invention. Area 601 includes several types of defined protocols that the user can select. The researcher is also able to create his own protocol. Areas of the screen 602-606 allow for the selection of the study, protocol type, target species, and tissue respectively. Area 607 allows the researcher to see the types of cells and other markers his cocktail or reagents will be able to determine are in the FACS run of his experiment. Area 608 allows the user to select the layout of the plates that the user wishes to use. This layout for instance may skip every row, skip every two rows or whatever the researcher wishes. There are also selections for calibrating, compensation, and using control samples that can be specified to be used with the experiment.

Figure 7:
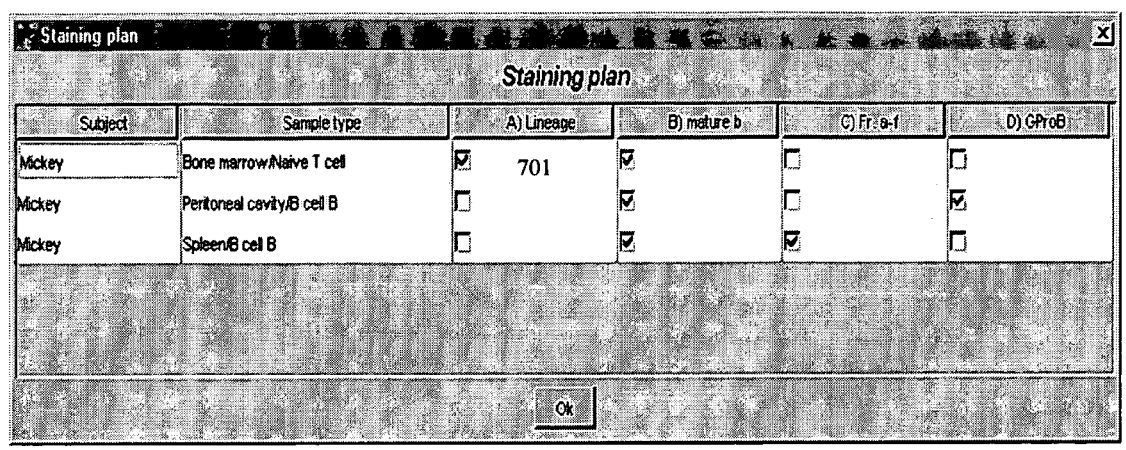
FIG. 7 is a display of a staining plan.

FIG. 7 is a display of a staining plan. This window also helps the user create an experimental protocol. The staining plan allows the research to view the subject and sample type of the specimens the user uses in the protocol. The staining plan also allows the user, in this embodiment with checkboxes, to select the features he wishes to stain for. For instance, in this example the check box 701 demonstrates the user wishes to stain for the lineage of Bone Marrow/Naïve T cells.

Figure 9:
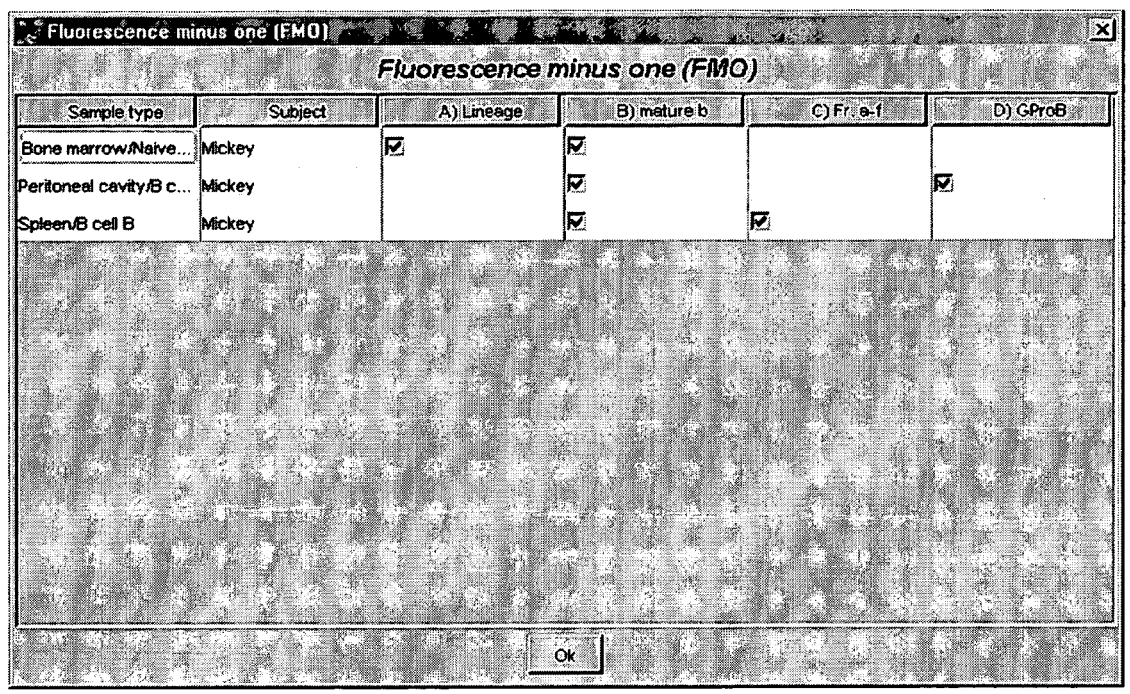
FIG. 9 is a display of Fluorescence minus one (FMO).
Figure 10:
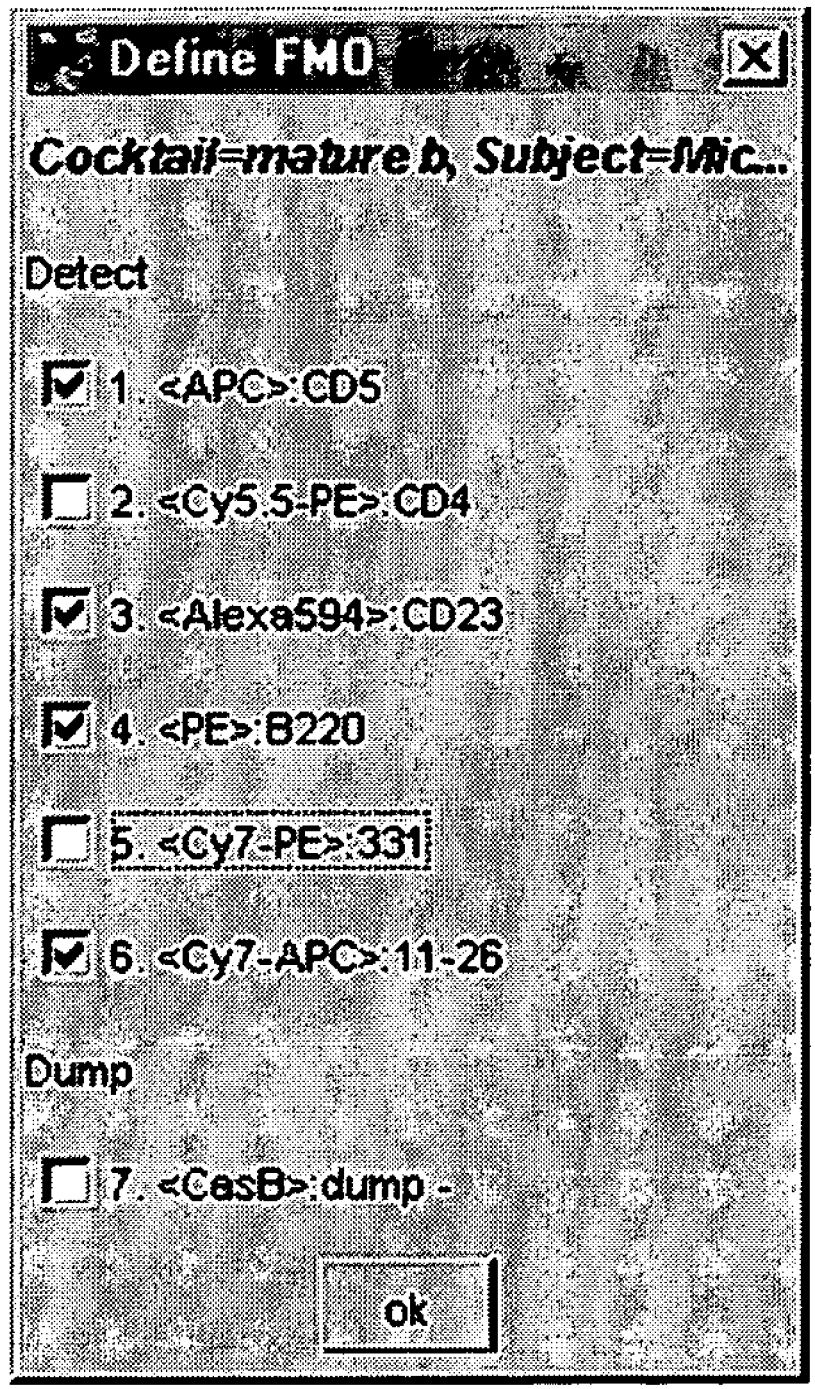
FIG. 10 is a display of the Define FMO window.

FIG. 9 is a display of Fluorescence minus one (FMO). This window is also used by the researcher to help create a protocol. This is a control to define the amount of fluorescence on a given detector on the given population that is intrinsically associated with the stained cell when no stain is presented for detection on the detector. This helps to determine both autofluorescence and inadequately compensated fluorescence. This then helps to determine the maximum signal over an unstained population. Compensation may be used to computationally or otherwise remove signal generated by autofluorescence or other unwanted signals. FIG. 10 is a display of the Define FMO window. This window allows the user to pick the FMO channel to consider with the user's experiment.

Appendix 1 includes a sample of the reagents for a sample study plus the decision process undertaken by the present invention to determine a feasible set of reagents for the study. Pages A1-A2 include a sample set of requirements a user uses while conduction an experiment. Pages A2-A18 includes an exemplary decision process the present invention undertakes to determine a feasible set of reagents for the experiment specified by the user in pages A1-A2. Pages A13-A18 includes a set of rules that the present invention uses in order to create a feasible experiment. Such a feasible experiment is demonstrated by the wells of FIGS. 11 and 12. The wells and the contents of the wells produced by the protocol maker may define the feasible experiment proposed by the protocol creator.

An example of a study is a clinical study. The study generally is designed to test one or more hypotheses. An example of a hypothesis is testing whether the number of CD8 T cells is correlated with the erythrocyte volume.

In the exemplary study, HIV-infected patients are recruited on the basis of meeting a series of entry criteria. Examples of such criteria are:

1) information collected directly by interviewing the patient
2) results of clinical analyses such as erythrocyte counts
3) results of FACS analyses such as number of CD4 T cells Experiments in the study may be conducted on samples from patients to determine whether the patient meets the entry criteria for the study. In this case, information and experiment results for each potential study entrant are stored in the study. The study also includes experiments such as staining cells from the patients with antibodies that reveal cells that express surface CD4 and analyses such as those that enumerate the number of cells expressing CD4. Relevant information about the subjects (patients) in the study is passed from the study to protocol wizards that help the user define the contents of experiments such as which samples from which subjects are examined. The study also allows the user to select from model protocols for the experiment to define types and the amounts of the FACS reagents that may be used. For example, once information for a subject is entered into the study, the study subject appears on a list from which the user chooses the samples to be examined in an experiment.

The study also includes the ability to specify that the protocol automatically send data that is collected to analysis programs and provide necessary information to enable the automated analysis to return specified results of the analysis to the study. Similarly, when these data are returned, the study may be triggered to specify automated analyses that return further digested results to the study. One result of this process is the automatic identification of subjects that qualify for further study by determining that the study criteria are met, such as the subjects' erythrocyte counts and CD4 counts are within the specified ranges. Further, the automated analysis includes the returning of FACS plots comparing CD4 and CD8 levels, the returning of charts with each subject's mean levels of CD4, CD8, erythrocyte counts, or other specified variables. The automated analyses also specify the performance of statistical procedures and the return of results of these analyses. In addition, the study includes methods for summarizing and displaying results of analyses. Finally, the study tracks samples to determine whether certain experiments were performed and specified data returned and may include information about the physical location of stored samples, the amount of the sample that has been used, and the treatment of the sample.

A basic research study may include samples from mice, information about the genetic makeup of the mice and references to genome and other databases relevant to the mice. It may also include information about the treatments that individual or groups of mice were given or may be given during the experiment and about the drugs or other materials with which the mice were or may be treated. The study also includes a timeline for treatment and, as above, defines protocols and automated analyses for collected data.

A FACS experiment in a study comprises staining cells with various fluorescent antibodies and running and possibly collecting cells through a cell sorter. A protocol maker helps the experimenter create his experiment by creating a suggested protocol for him to follow. The protocol maker may ask the researcher how many different stains he wishes to use to mark various structures. These stains may, but do not necessarily need to be stains for different structures. Typically the stains are fluorescent conjugated antibodies. The user then informs the protocol creator which structures he wishes the stains to mark and the present invention responds with an offer of a series of "option" lists from which the user selects the type of cells and the specific reagents to be used in the experiment. Option lists may include generic types of cells or cells and samples specified in the parent study to which the experiment belongs.

The present invention then asks the researcher which FACS machine he plans to use. Each FACS machine could be equipped with different lasers or light filters enabling different FACS machines to collect data for antibodies labeled with different fluorescence "colors". The wizard then determines whether the FACS machine specified by the user is able to take data for the fluorescent reagents selected in the protocol. Alternatively, the present invention suggests which of the FACS machines available to the user can be used. In either case, the wizard then assists the user in scheduling an appropriate analysis time period on an appropriate FACS machine.

The protocol is created with information from the Protégé ontology. A partial sample of this information is shown in FIGS. 14-17. The present invention then use a series of rules to create a feasible protocol. Some possible decisions and rules the present invention uses and performs are displayed in appendix A. These include making sure that the antibodies selected emit at different wavelengths as well as making sure that the FACS machine selected to perform the analysis and/or sorting is capable of exciting the antibodies so that their emissions are received.

Finally, the protocol creator uses combinatories or other procedures to define the reagent and cell sample combinations that the user pipettes (add to tubes) to complete the experiment and create a protocol for the researcher to follow. The combinatories may also use a depth first search to determine which reagents are feasible to add to the protocol. The protocol maker also specifies the control tubes that are to be used and provide the concentrations and amounts of antibodies to use, the dilutions of the antibodies, the various steps to perform, the various centrifugations to perform, and the FACS to operate. Typically a control tube is suggested for each antibody employed in the study. Further a blank control tube for each separate organism is suggested to determine autofluoresence. Appendix A demonstrates a set of rules and decisions the present invention uses to create a protocol.

In one embodiment of the invention, the system uses a knowledge base to determine the protocol to use. Though any type of experiment may be implemented with the system, the following example is for a FACS experiment. A FACS protocol may be set in the Protégé code to include one or more cocktails of reagents. The cocktail elements include a) one or more channels and b) one or more gene expression reporters. The channel corresponds to an optical band that the cytometer detects. Two types of channels are dump channels and detect channels. Dump channels are where the optical filter is desired to identify one or more antigens/specificities (a cocktail includes one or more of these). A detect channel is where the optical filter is desired to identify a single antigen/specificity (a cocktail includes zero or more of these). There also are zero or more gene expression reporters. The protocol maker also ensures that a) each channel only has one fluorochrome, b) for the same cocktail, the same fluorochrome or spectrally-equivalent gene expression reporter is not used twice and c) for the same cocktail the same specificity is not used twice in a dump or detect channel. The system also gives priority to those fluorochromes preferred or attempted to be selected by the user. The system chooses from a list according to the scientist's priority while taking into account the current inventory. Further, other constraints such as cost are taken into account. Additionally, the scientist directs the system to use a specific reagent lot from the inventory as well as a specific dilution for a typical FACS experiment or for a titration protocol experiment. Last, the system determines which FACS machines would feasibly work with the fluorochromes selected for the cocktails and also take into account the user's preference for a particular FACS machine. Again this information is retrieved from the knowledge base.

The reagents used by the protocol have attributes associated with them. These attributes include the reagent's distinguished name, Clone ID, Common name, Specificity, Titre, Fluorochrome Name, Fluorochrome Lot number, and concentration. The user is prompted to select the reagents used through a "Reagent Palette". Such a palette includes a catalog of reagents in stock, pre-determined sets of reagents typically used in similar protocols, and an ability for the user to enter a new choice of reagents for the experiment.

The protocol creator also performs various tasks behind the scenes to create a valid protocol for the researcher, to call for pre-packaged analyses, to check data quality during data collection, and to display the information about the reagents and cells in a sample at the time of data collected or any other time.

The protocol editor may be tied to a database to enhance its, as well as the researcher's efficiency. In the previous example, several items may be used from the database to create the FACS protocol. For example, 1) The database may hold data for the fluorescent recognition abilities of all of the FACS machines available to the user. This allows the protocol editor to select only those reagents that are available to the user and can be viewed by the FACS chosen by the user. There are a wide variety of possible combinations of possible reagent choices that can be selected. Specifically, there are be $n!/(n-k)!k!$ possible reagent choices where n is the total number of fluorescent "colors" that for which the FACS can collect data and k is the number of stains used in the FACS experiment. However, this number is restricted because not all reagents are available in all colors.
The present invention also provide a novel way to enhance the effectiveness and speed of the selection of the reagent combination by applying well know combinatorial techniques and depth-first search in a new way to this biological problem. This function is performed by recursively selecting one reagent at a time. If the most recently added reagent cannot be used with the current set, then that reagent is removed from the list of suggested reagents. The algorithm runs until a set of usable reagents is determined.

2) The protocol creator also consults laboratory databases to determine how much of each reagent is available to the user. If the protocol creator finds that the amount of reagent available is below a pre-set threshold, it automatically indicates the reagent shortage and suggests another combination to be used. The protocol creator also consults the database as to the effectiveness of each stain to bind to the type of cell being used. It then uses a greedy or another algorithm (such a s the ones suggested to select reagents combinations) to select an optimal set of stains to be used in the experiment. Other factors taken into account for this optimization include the price of the reagents, the temperature compatibility of the reagents in a given combination, and the resolution possible for target cell surface or internal markers when stained with the selected reagent combination. This may be performed using a scoring function that provides a score for each of the factors in selecting the reagents.

3) The protocol creator suggests the layout of the wells, tubes, or containers used to perform the experimental protocol. The layout depends on the proximity of like samples, like reagents, and controls. The layout also is created to minimize the movement of the person undertaking the protocol. Such an instance would be when several tubes require the same regent cocktail. In this case, it would be of benefit to have those wells, tubes, or containers located near one another. The protocol editor also suggest the creation of reagent cocktails when several reagents with the same proportions are used in various wells, tubes, and containers. The reagent cocktails are designed by determination of like reagents used in multiple wells. This determination may be through linear programming or another optimization routine designed to minimize the number of pipetting steps or any other experimental concern such as time, cost, or ease. The constraints for such a linear programming model include any of the aforementioned factors contributing to experimental time, ease, or cost.

Figure 11:
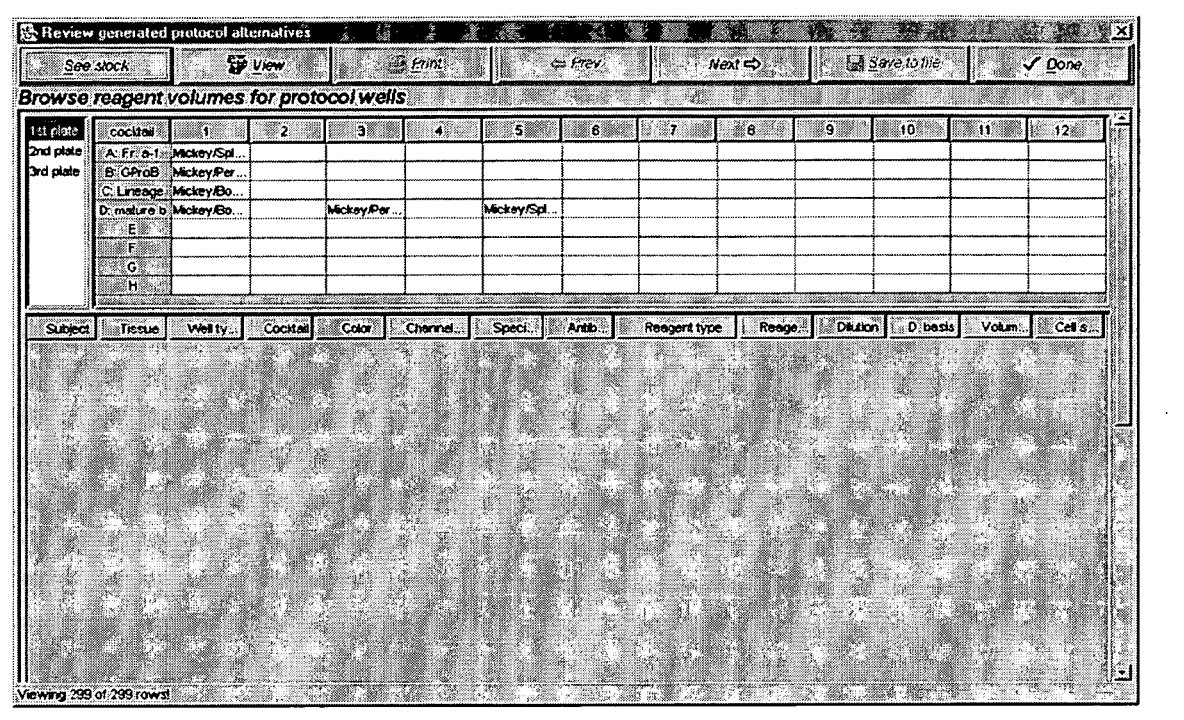
Figure 12:
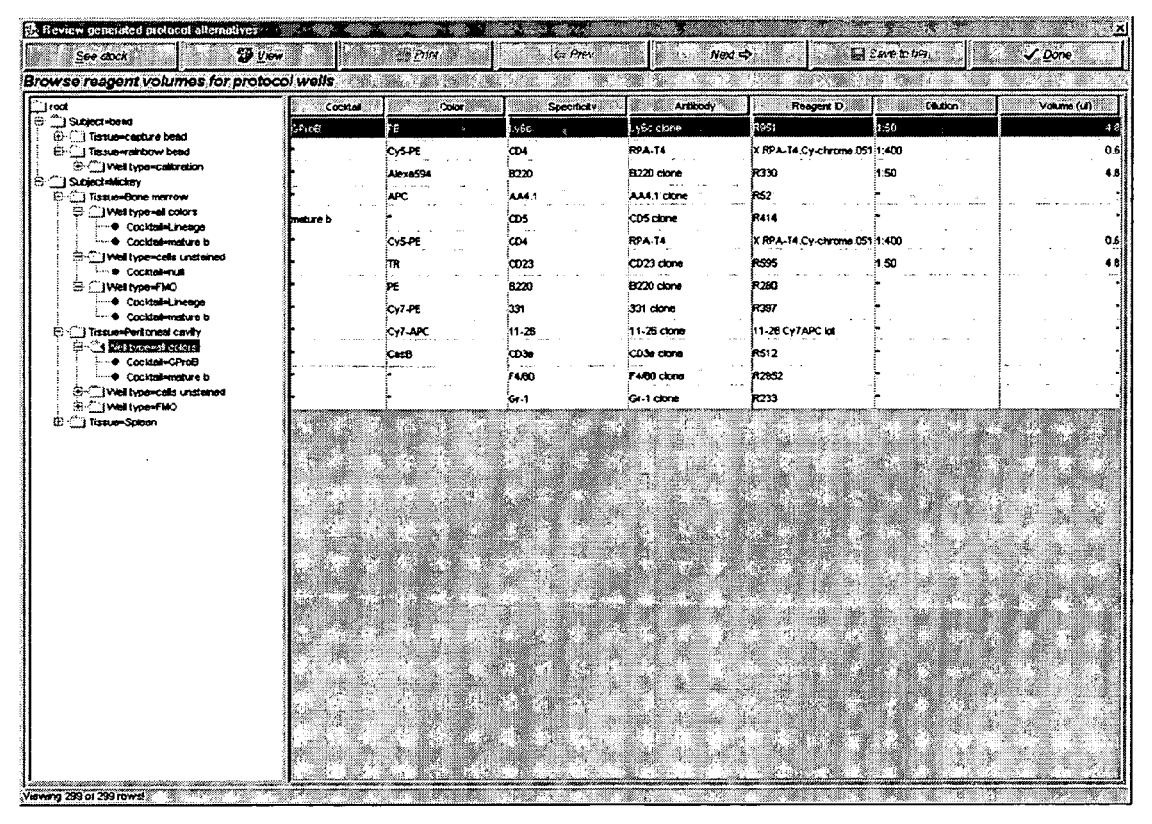
Figure 13:
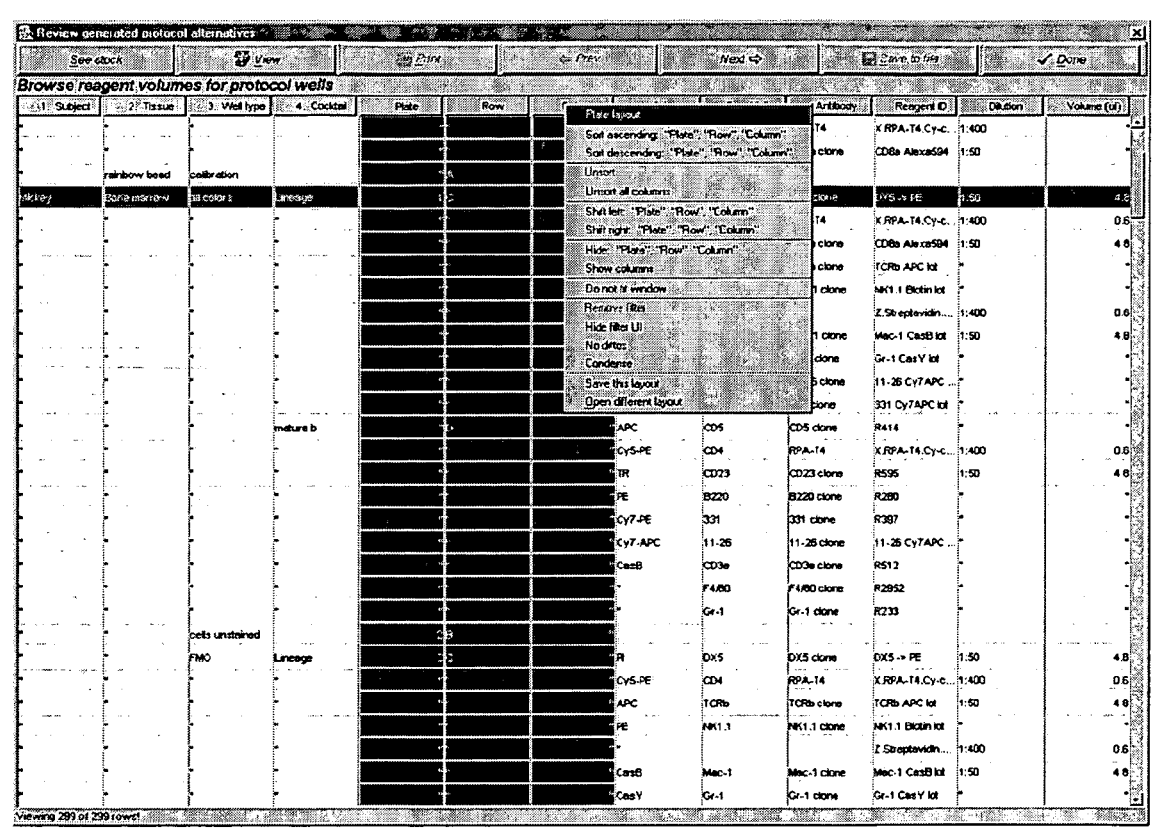

4) The protocol creator also suggests the use of different FACS machines that are capable of performing the experiment because either the FACS machine is cheaper to operate or the cost of the reagents for that FACS machine is cheaper. The protocol creator also anticipates what type of data is collected and prepares table and charts to be filled in after the experimental data is collected. One method of creating charts is to create 2-axes graphs for all the pairs of data that the protocol is expected to collect. FIGS. 11-13 describe to the research a possible protocol that the present invention creates based on the inputted options selected by the user constrained by the rules and inputs to the knowledge base. FIG. 11 is a display of generated protocol alternatives. This screen allows the user to review the well created by the protocol maker. It also displays the cocktails as well as the specimens that should be put into each well. The page also allows the user to view multiple plates by selection of the different plates in area 1101.

FIGS. 11 and 12 present the user with a display of the wells in a plate and the contents of those wells. The rows of the table correspond to different wells of the plates. Each well includes information for the subject, tissue, well type, cocktail, plate, row, column, color, specificity of antibody, source of antibody, reagent ID, preferred dilution and volume.

FIG. 12 demonstrates that a table may be sorted sequentially by a series of columns and condensed either into a summarized table or a condensed tree structure that can be opened to visualize table elements. The tree of the condensed table can be connected to the full table by active links such that selecting an item in the condensed view exposes full information about the item in the full table. This explains a general concept of viewing data in a full table by condensing to tree or condensed table views while maintaining active links to the full data in the table.

Protocol Storage

After a protocol is created and/or used, the protocol creator then allows the user to store and re-use the protocol in the database under the current study or any other study the scientist wishes to use the protocol for. Once data collection for a sample is complete, the protocol creator cooperates with the data collector to couple the collected data with the annotation information (reagents, cells, treatments) known to the creator and sends the coupled data and annotations to the database for permanent storage and archiving. Once the data collection for a full experiment is complete, experiment-related information (standards, machine conditions, etc) are sent to the database to be coupled with the sample data and annotation. These couplings are accomplished by storing the data separately from the annotation data and associating these items permanently by use of non-volatile pointers or some other means. The parent study also is informed of the completion of the experiment and the location of the output from the experiment (protocol and data collection).

Protocol Implementation

FACS

After the scientist creates the protocol, he is now able to perform the protocol and conduct the experiment. This experiment creates data that is automatically captured by the database, coupled with the annotation information in the protocol, transferred from the machine used to collect the data (FACS, in the example above) directly to the proper location for the particular experimental data. This can be performed in several ways, including the use of LDAP, XML and XSL style sheets. Analysis programs automatically perform preliminary analysis specified by the protocol or elsewhere. The protocol editor determines the nature of data and informs the analysis program the type of data that is represented. The data types include nominal, ordinal, or continuous that are either dependant or independent variables. The variables may also be crossed or nested. These analyses are informed by the annotation and possibly other information associated with the data (such as data type) collected for each sample. Results from these preliminary analysis are stored and associated with the collected data and be locatable via an experiment data tree that is available for the experimenter to view. For FACS analysis the collected and annotated data is automatically be sent to a FACS data analysis program such as FloJo or CellQuest. Once FACS analysis begins, the analysis software suggests possible gating strategies with the use of clustering algorithms or other artificial intelligence techniques. Further gating data is displayed using the annotations from the protocol editor to determine the labeling of the axes of the displayed data. The data also is sent for analysis to a statistics analysis package such as JMP (from the SAS Institute). The data is also automatically processed to determine such statistics as median attribute values and standard deviations of attribute values.

Gel Electrophoresis

As with any other scientific or engineering method, Gel electrophoresis may also be incorporated into the current system of protocol development. For instance, the protocol maker prompts the user to select/input the type of gel that is to be run. These gels include a Northern or Southern blot. Further, the protocol maker prompts the user to input the number of lanes in the gel and select the sample is to be placed in each lane. The sample may be defined at the protocol level or may be selected from a list generated from information already entered into the study to which the experiment protocol belongs. Further, the protocol maker, possibly informed by the study, prompts the user to determine which type or types of standard controls, such as ladders, are going to be used in the experiment. The protocol maker also suggest the lanes that each specimen should be placed in according to rules pre-defined for the type of gel and sample in the experiment.

After the experiment is completed, the user brings the gel to an instrument for automated or manual data collection. For instance, the user brings the gel to an ultra-violet gel reader connected to a computer. The reader takes a picture of the gel and send a digitized version, coupled with the protocol information that describes the sample and the experiment, to a central data store for archiving. The gel reader then sends the digitized picture to an analysis program. Alternatively, the data in the data store is sent at the user's request, to the analysis program. This analysis program, for instance, could determine the size of each fragment found in the gel by comparing their positions to the positions of the ladder. The results of the analysis are then archived in the database for later retrieval, further analysis or abstraction into summaries in the parent study. The parent study is also informed of the completion of the experiment and the location of the output from the experiment (protocol and data collection).

Experimental Models

There are several experimental models which may be incorporated into the database. These models are be selected by the user to provide the protocol creator what type of experiment to create. The experimental models include:

1) Crossing Model: Many experiments are essentially combinatorial, i.e., this set of reagents or reagent cocktails is applied to each sample in a group of samples. Typically it corresponds to some N×M grid of wells in the staining plate. An experiment might have 1 or more of these repeated sets of reagents.
2) Titration Model: The user specifies a target sample and a reagent and then a range of dilutions 2, 4, 8 . . . or 10, 20, 50, 100 being typical. The layout of the dilution is a single column, a single row, or otherwise on the plate or other type of container.
3) Screening Model: The user specifies a reagent cocktail and a large number of samples which are quasi-automatically named.
4) Fluorescence Compensation Controls Model: For each dye (or dye lot) which occurs in an experiment model, the user or protocol editor specifies a sample to be used as a control. Usually the control will be one of the samples which is stained with the reagent.
5) Unstained Controls Model: The user or protocol editor defines an unstained or negative control for a protocol involving staining. Unstained controls and fluorescence compensation controls may be coupled together in a single experimental protocol to create a population of suitable controls.

The protocol editor creates a GUI representing the wells, tubes, or other containers holding the reagents and samples. The user is able to "drag and drop" the sample or reagent to another well, tube, or container to alter the experimental protocol the user created or the protocol creator suggested.

Hypothesis Testing

After the study is completed the software is capable of testing the hypothesis stated in the study protocols. The hypothesis may be test by combining the statistical information gathered during the experimental protocols and determining if they fit the hypothesis. This determination also may be done manually by viewing the data or automatically by allowing the data to be analyzed by a data analysis package such as JMP. In one embodiment, JMP automatically analyzes the data that was specified by the user when the user creates an experimental protocol with the appropriate wizard. The wizard then associates the expected data with the study node with so that the hypothesis is automatically be tested. In another embodiment, an automatic clustering program is used to analyze the data. The results of this clustering program are displayed to the user automatically or upon request of the user.

The database allows access to the data for several purposes. First, the user is able to provide hyperlinks to collected data and experimental protocols so that others may access the data and protocols. Others that would access the data include collaborators, reviewers, and others reading published articles including hyperlinks to the data. Second, the database acts as a cell surface expression library enabling people such as researchers and clinicians to facilitate diagnosis and definitions of new conditions by comparing the data from the database with locally collected data.

Database

Knowledge Base

Figure 8:
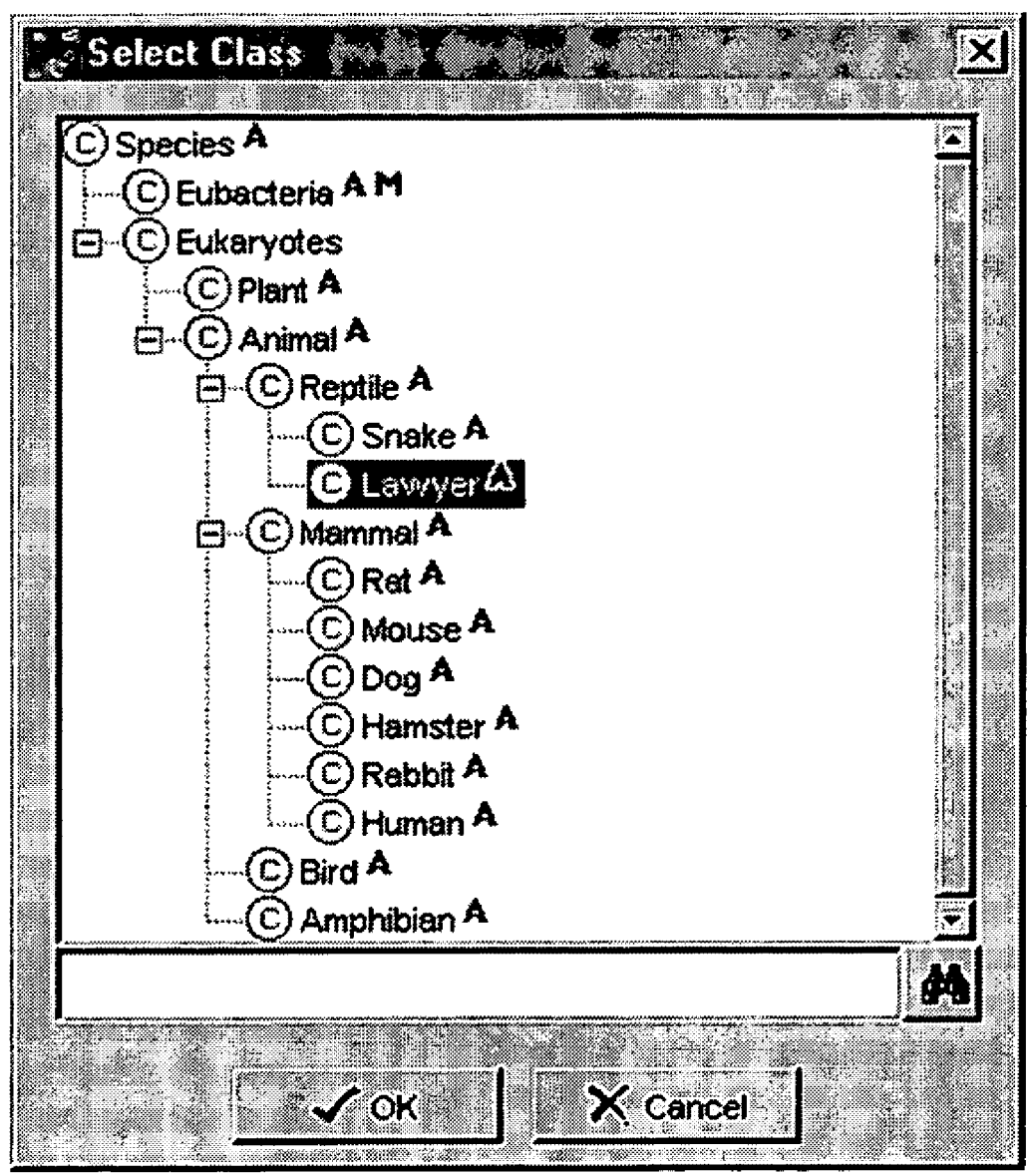
FIG. 8 is a display of a tree of the ontology the present invention is capable of creating in order to represent the data and knowledge.

In one embodiment, the database is constructed as a knowledge base. One such knowledge base is a Protégé ontology knowledge base. FIG. 8 is a display of the tree the ontology of the present invention is capable of creating in order to represent the data. The tree is capable of holding various information for different species. For instance the current embodiment has information for several mammalian species including rats, mice, dogs, hamsters, rabbits, and humans. If the user selects one of these species the present invention will use its knowledge base for that species when creating protocols. It will also save results to the species selected. The knowledge base is created with information from various sources. The following figures provide an understanding an understanding of the creation and update of a Protégé ontology of the present invention.

Figure 14:
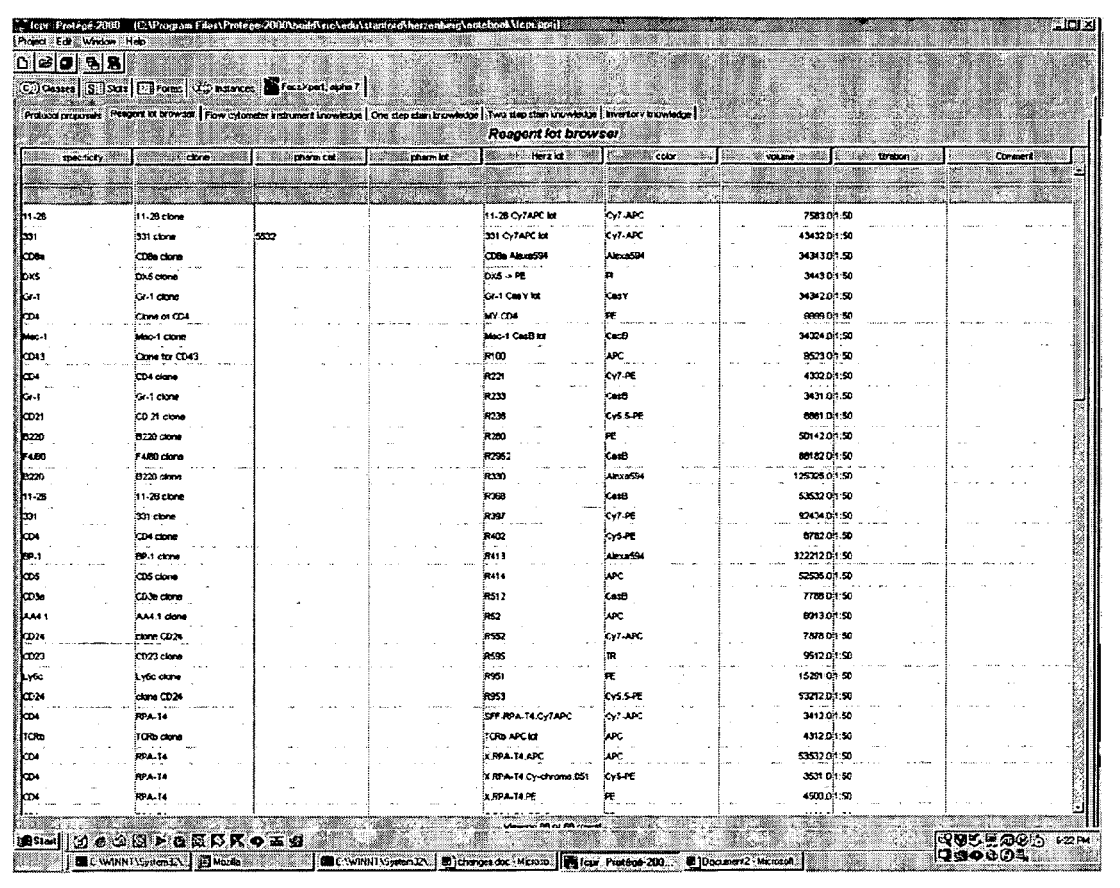

FIG. 14 presents the user with a sample window of reagents. The window displays those reagents that were added to the ontology knowledge base. This information is stored to and retrieved from a Protégé knowledge ontology. The information for each reagent includes specificity, clone, catalog number, lot number, internal lot number, color, volume and titration. The window also allows for comments to be entered for each reagent.

Figure 15:
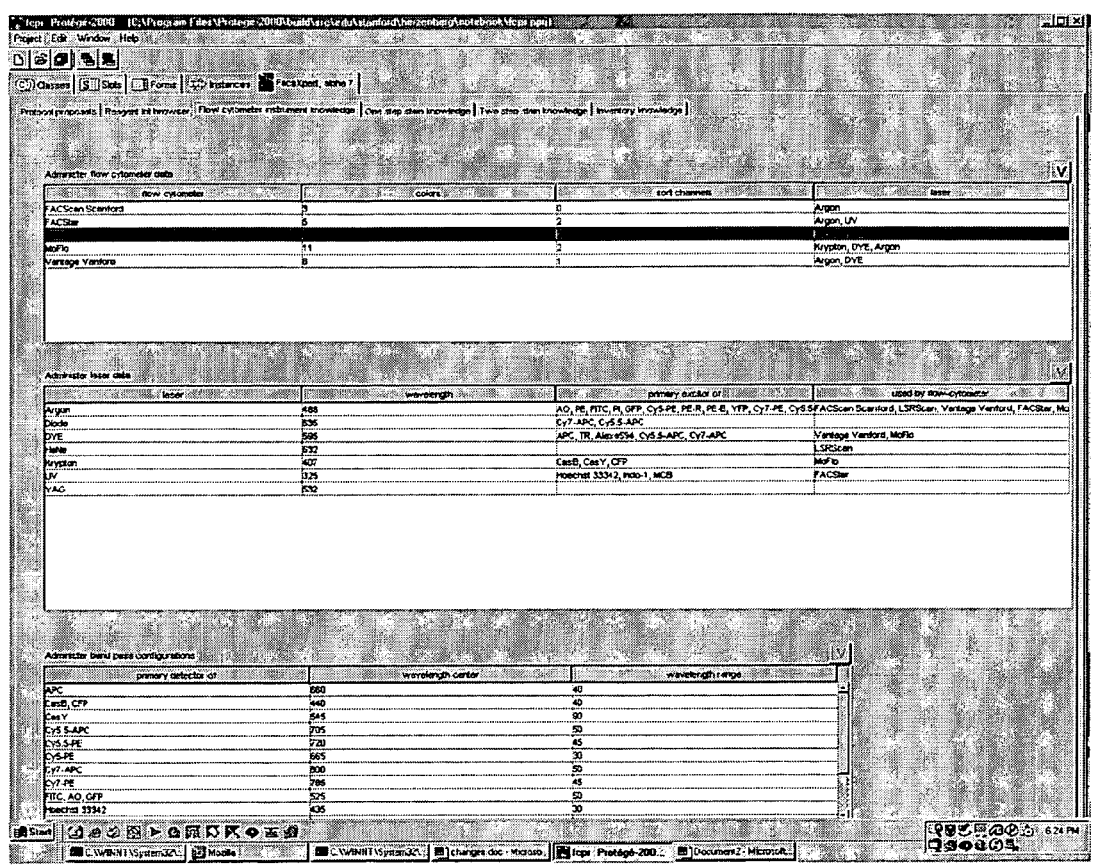
FIG. 15 a window which may includes information about the FACS machines available to the user.

FIG. 15 presents the user a window that includes information about the FACS machines available to the user. This information is stored to and retrieved from a Protégé knowledge ontology. The screen includes the name, number of colors, number of sort channels, and the type of lasers for each FACS machine. The window also include data for each type of laser including its type, wavelength, primary target fluorochromes and FACS machines in which it may be found. The window also presents data for each fluorochrome including its type, wavelength center and wavelength range. This information is stored to and retrieved from a Protégé knowledge ontology.

Figure 16:
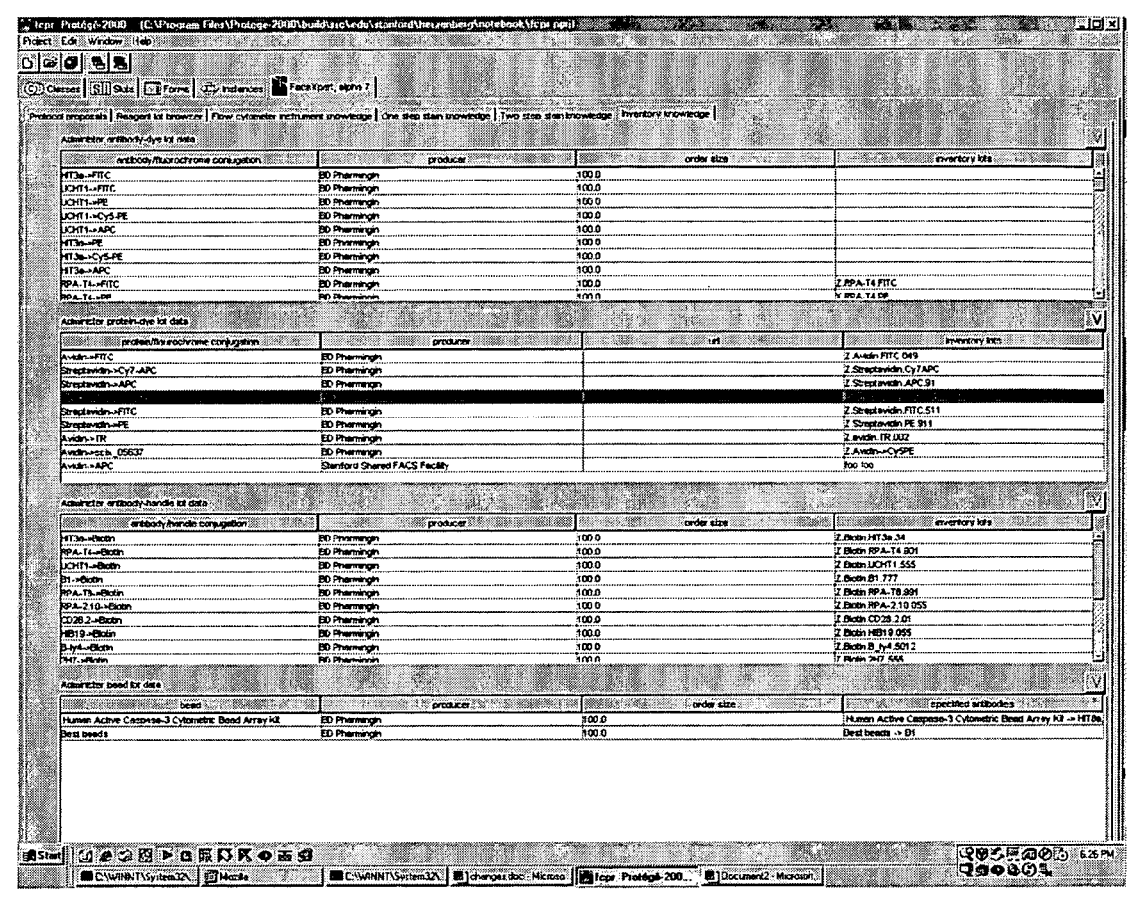
Figure 17:
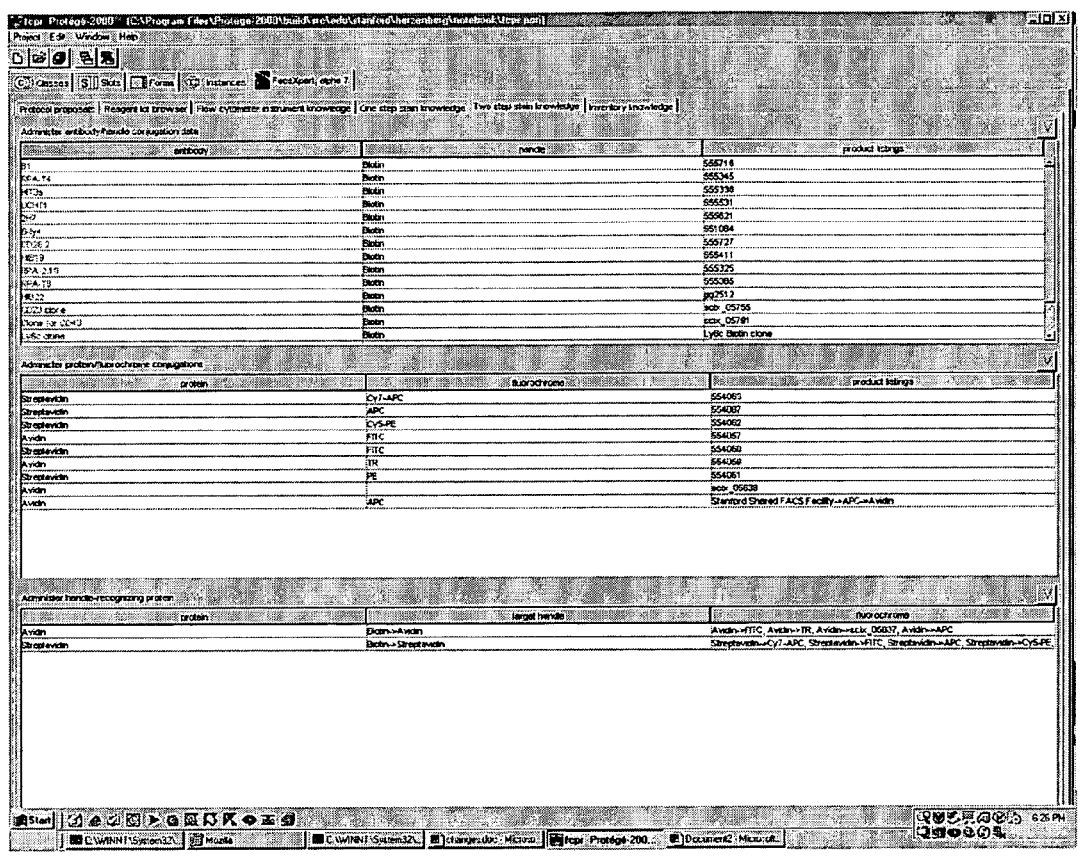
FIG. 17 a window that provides information regarding specific molecular pairs and other reagents.

FIGS. 16 and 17 present the user a window that provides information regarding specific antibody-fluorochrome pairs and other reagents. This information is stored to and retrieved from a Protégé knowledge ontology. The window provides antibody-dye lot data including conjugation, producer, order and lot. The window also provides protein-dye lot data including conjugation, producer, order and lot. The window also provides antibody-handle data including conjugation, producer, order and lot. The window further provides bead data including bead, producer, order and specific antibody. The window additionally provides information regarding antibody/handle conjugations including antibody, handle and product. The window also provides information regarding protein/fluorochrome conjugations including protein, fluorochrome and product listing. Last, the window provides handle/recognizing protein data including protein, target handle and fluorochrome.

Figure 18:
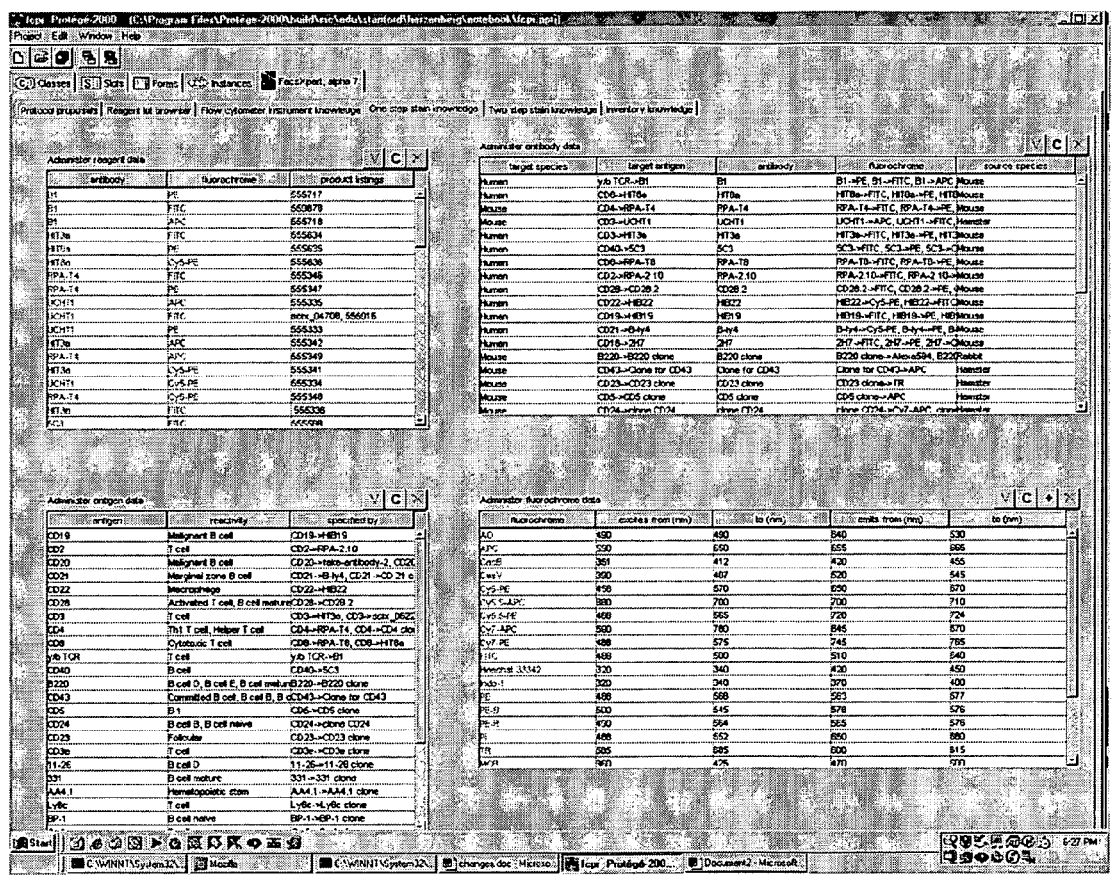
FIG. 18 a window to show at least a portion of the stain knowledge stored in the Protégé ontology.

FIG. 18 provides a window to show at least a portion of the stain knowledge kept in the protege ontology knowledge base. This knowledge includes reagent data, antibody data, antigen data and fluorochrome data. This window also provides the ability to add data or change data to the protégé ontology knowledge base. The data alteration is performed by altering the data in the window or creating new lines to enter new data into the window.

Figure 19:
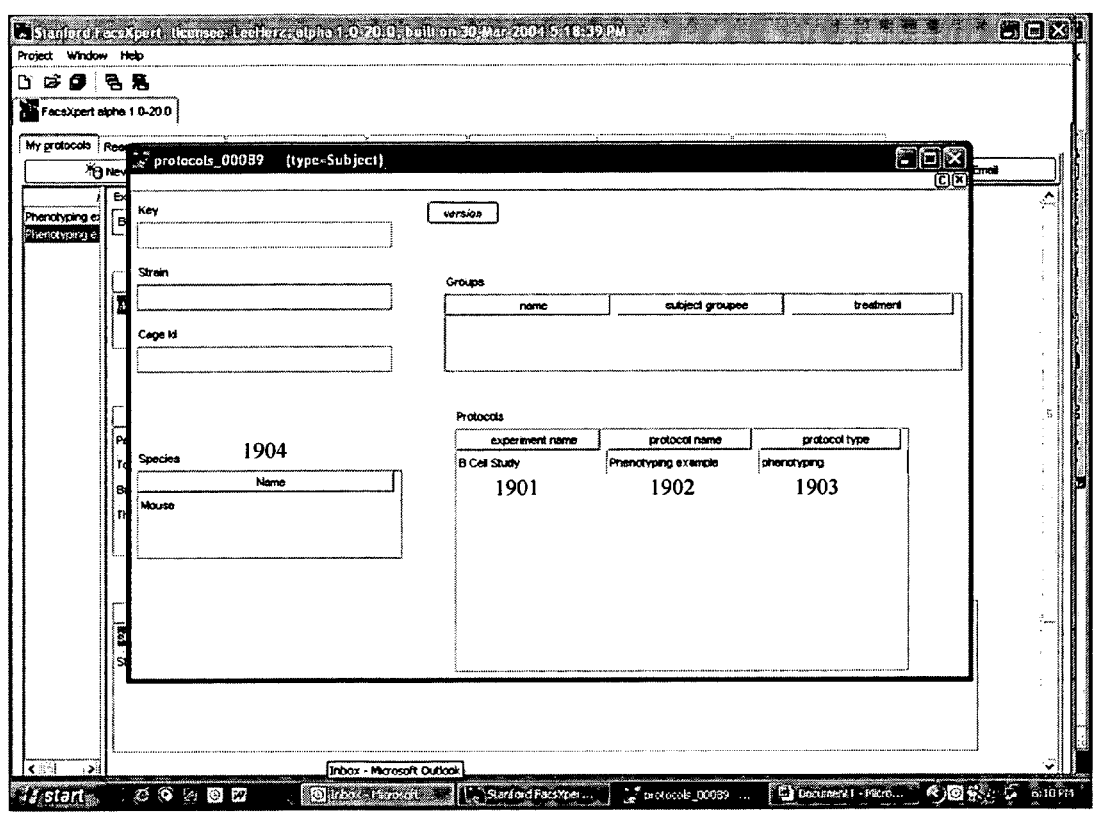
Figure 20A:
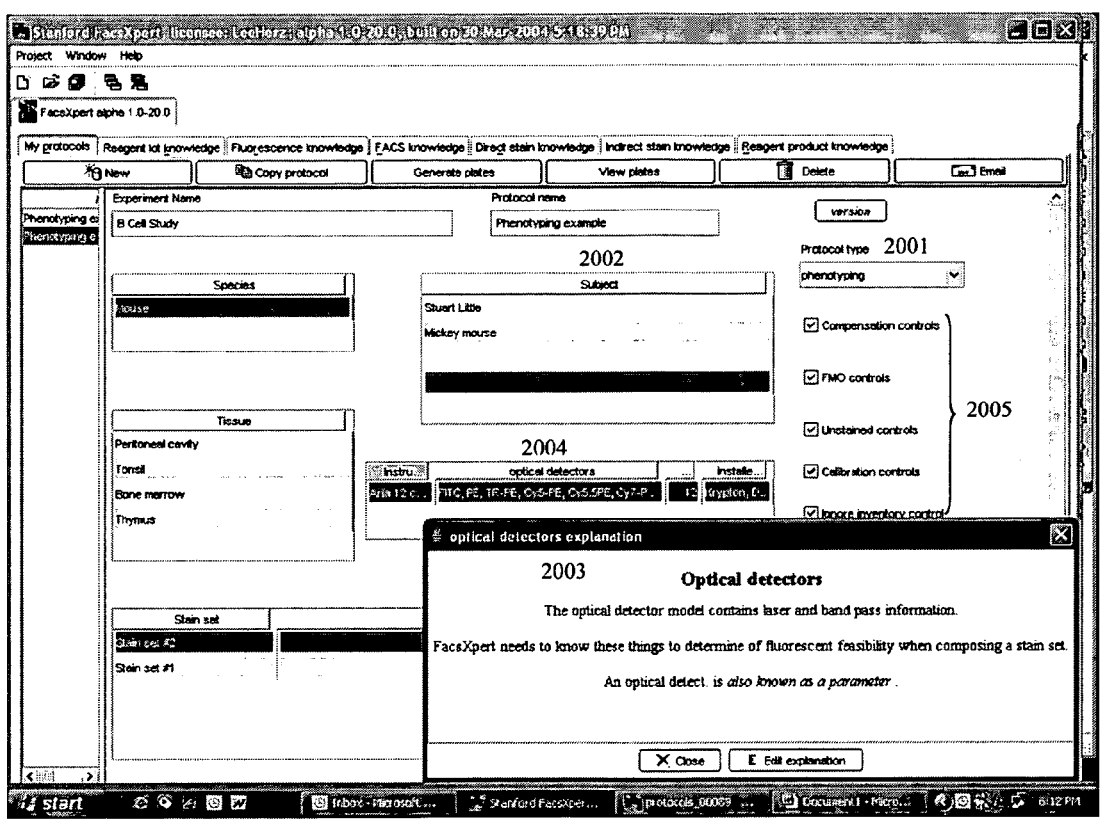
Figure 20B:
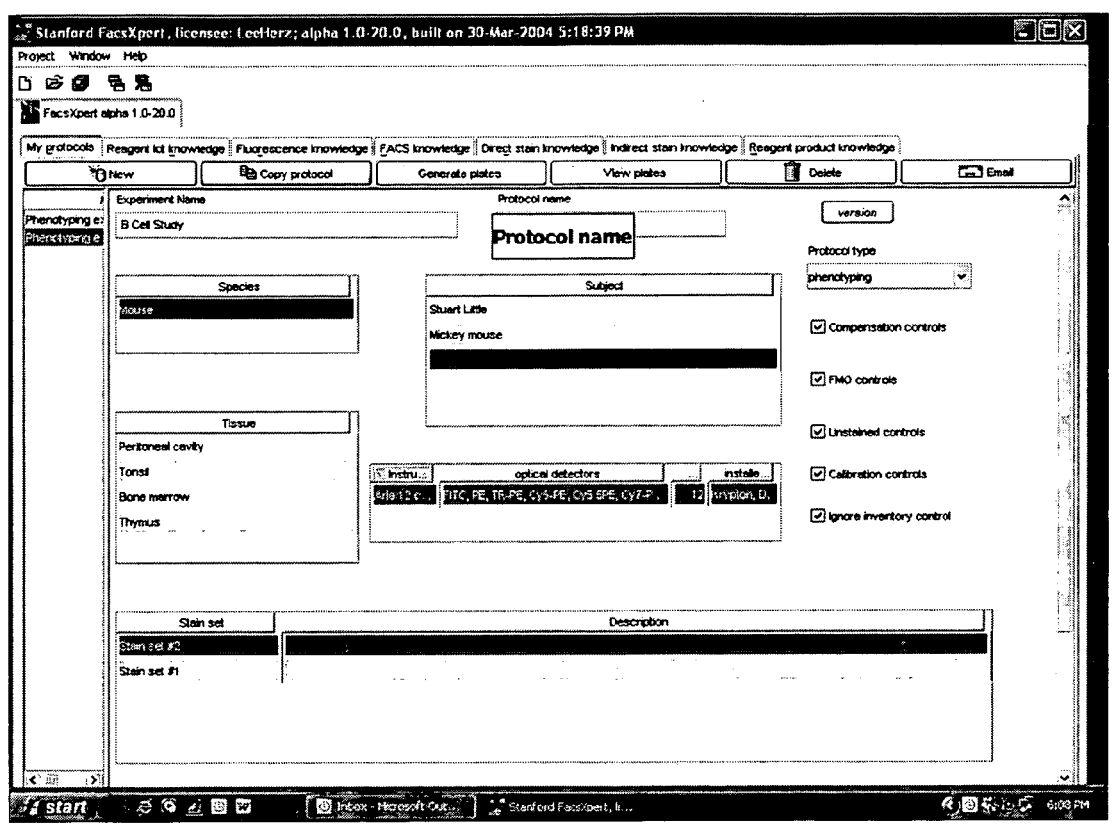

FIGS. 19-26 describe another embodiment of the present invention. FIG. 19 is an opening screen one views when one begins the graphical user interface of the present invention. The GUI shows the experiment name 1901, the protocol name 1902, and protocol type 1903. The user may manually alter these fields within the GUI. The user also select the species 1904 to use in the experiment from a list of species that have been entered in the knowledge base. The user selects from the subjects entered in the knowledge base and can also add subjects to this. FIGS. 20*a* and 20*b* are a GUI new subject menu. The GUI takes as input a key which includes an identifier stain if the subject is a mouse mice or subject, id number, or chart number if the subject were human.

The GUI allows editing and constructing a set of stains each of which has a fluorescence color attached to it. The system constructs a set of stains that detect the determinants that the user wants (those that are on the surface or inside of the cell) and that can all work together so that the set of stains can be detected by a flow cytometer that can detect a certain group of colors. The knowledge base includes the information about stains, determinants and flow Cytometry instrument capabilities. The system access this information in assisting the user in composing stain sets.

The interactive protocol field 2001 informs the user of the protocol type. Interactive subject field 2002 informs the user of the subjects of the protocol. In this example the subject added are Stuart Little and Mickey Mouse. Underneath the subject menu there is a menu for optical detectors 2003. It provides information to the user on how to use the optical detector input field 2004. The system also includes informational messages for entry points and other areas of the graphical user interface.

There is a series of interactive check boxes 2005 that indicate the kinds of cell and reagent controls the user wants to have implemented in the experiment. If a corresponding box is checked, then the system will automatically include compensation controls, which are singly stained samples or beads, or examine the spill over of fluorescence due to spectral overlap of the fluorescent stains (these are "fluorescence minus 1", or FMO, controls stains in which one of the reagents is left out of the cocktail). There is also a check box for unstained controls that serve to indicate the amount of autofluorescence associated with cell samples. The calibration controls are beads that let the user set-up, test and calibrate the machine.

The system helps the user compose stains sets, which are collections of fluorochrome-coupled reagents that are combined in order to stain the cells and determine reactivity with proteins, carbohydrates or various surface features of a cell. Reagents can be combined in one cocktail to allow simultaneous surface and intracellular staining and/or staining for chemicals that are in the cell.

Figure 21A:
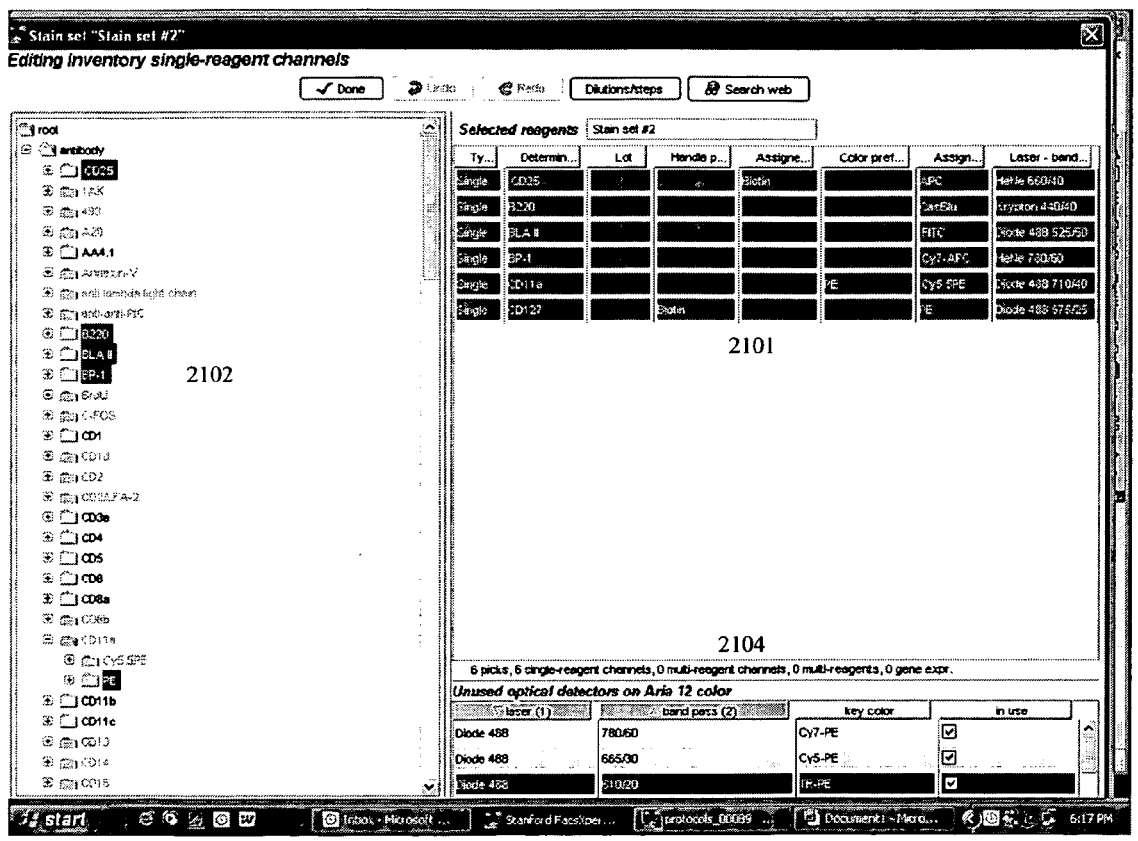
Figure 21B:
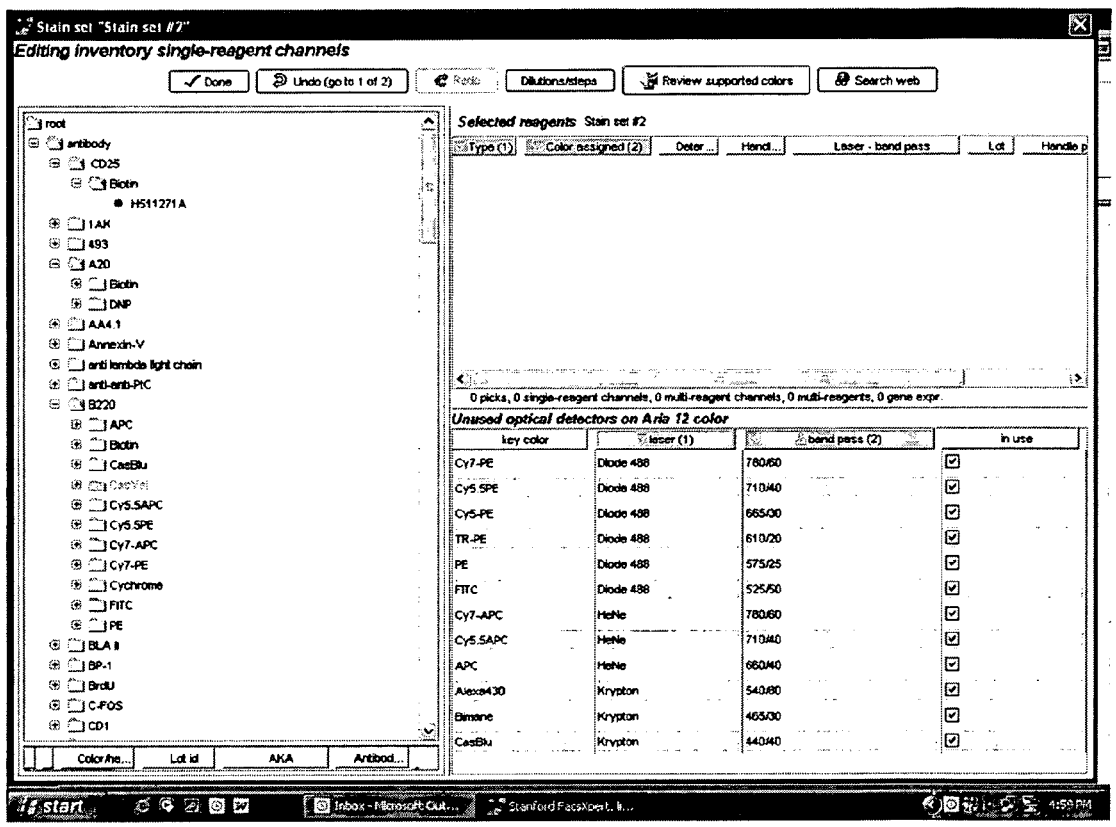

The stain set may be interactively specified and edited within the GUI. FIGS. 21*a* and 21*b* are GUIs of a chart and tree showing the reagents (determinants detected and associated colors) are present in the user's inventory. The reagents that are available for use with the optical detectors on the flow Cytometry machine that the user has chosen are shown as active. Those reagents in the inventory that cannot be used in the experiment are shown as "greyed" out.

As the user makes selections, the available reagents (not greyed out) are progressively constrained to fit with the optical detectors for which a color has not yet been chosen. The menus also allow the user to "edit" the selected reagents by either selecting/deselecting them in the tree 2002. This helps the user rapidly select a feasible set fluorescent reagents to use with the optical detectors on the chosen flow cytometer. The knowledge base, which has knowledge of the fluorescence properties of the reagents and the capabilities of the flow Cytometry machine that the user selected, provides the information that the system used to update and inform this display.

A reagent chart 2101 that shows the selected reagents and their properties is also shown in the GUI. The system updates the chart so that the information is maintained in synchrony with the tree. A second chart 2104 shows the flow Cytometry detectors that are as yet unused by the reagent selections. This chart is also updated as reagent selections are made with the tree. The chart combines a subject with the tissue obtained from a particular subject with a stain that is defined by the user or the knowledge base.

Figure 21C:
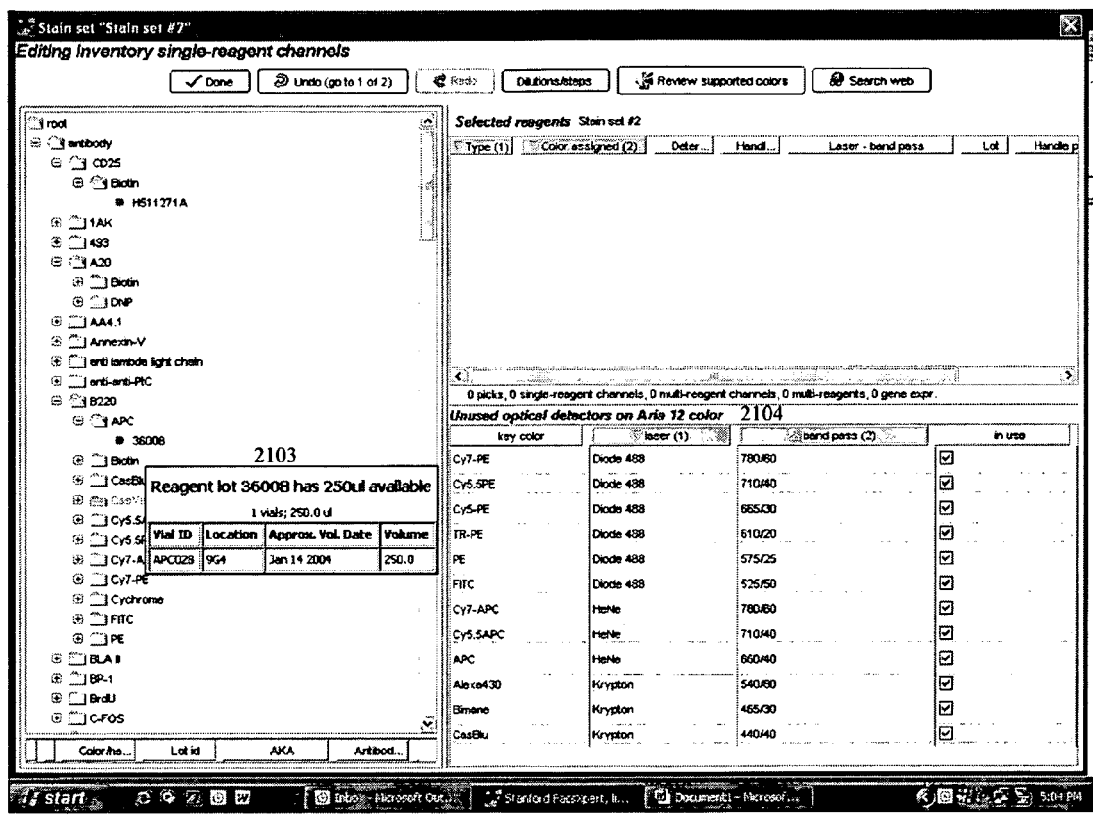
Figure 21D:
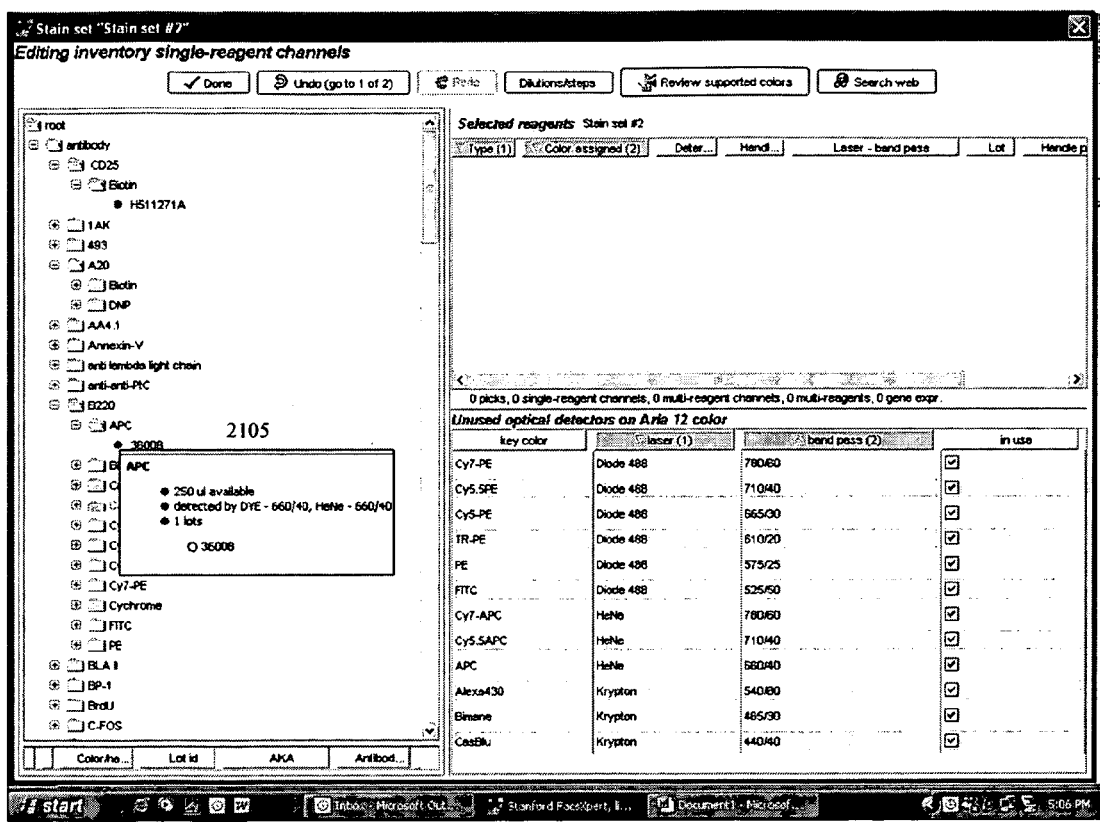

FIG. 21C shows a view of the GUI with folder B220 open. Box 2103 opens in response to a user action, such as clicking on 36008, and shows the reagent information corresponding to the 36008 lot of B220-APC. This information is retrieved from the knowledge base when it is presented to the user. The user further inputs information into the table to update the knowledge base if so desired. The lots of reagent displayed correspond to the lots of reagent in inventory as determined by the system interacting with the knowledge base. Chart 2104 shows the available optical detectors or other machines (such as microarrays) available to perform the protocol. FIG. 21D shows table 2105 which provides the user additional interactive information related to the reagent. This information is also retrieved from the knowledge base.

Figure 22A:
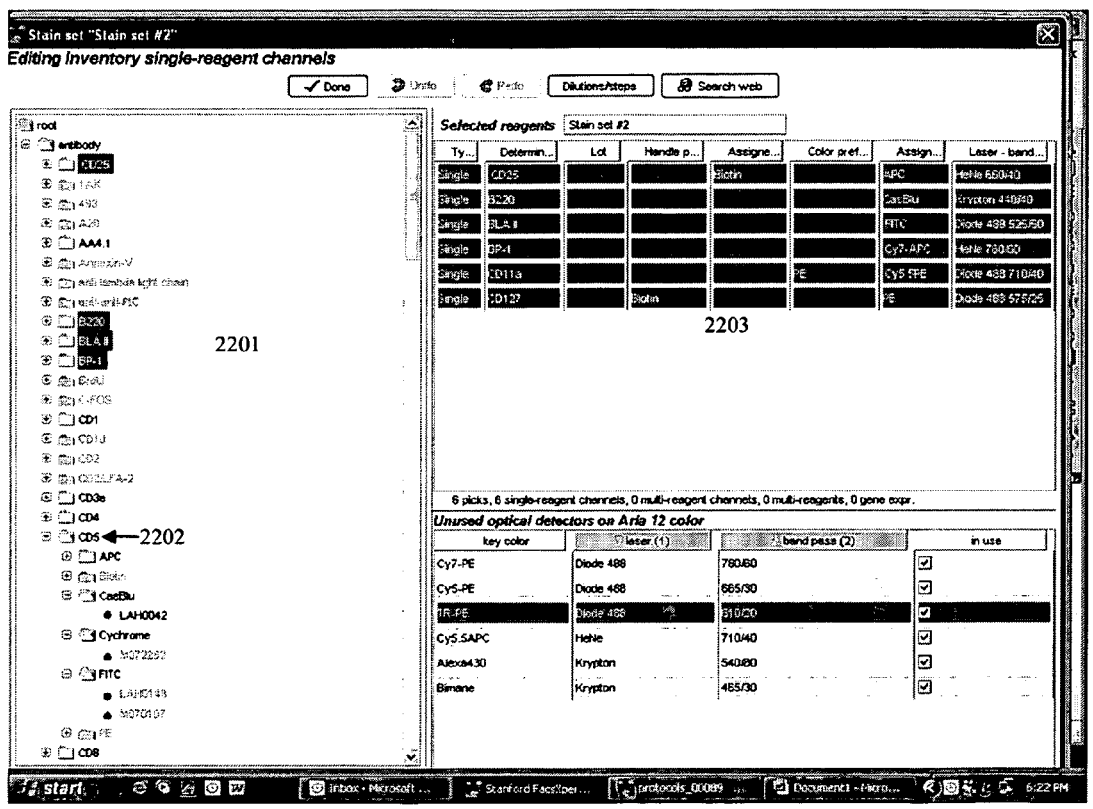

FIG. 22*a* shows a GUI with an incomplete experiment protocol. On the right hand side are a series of rows in a chart, each of which represents a particular determinant detected by a reagent. As an example, column 2 in the chart shows the determinants to be CD25, B220, BLA2, etc. The tree 2201 on the left includes reagents sorted by letter and number. In this embodiment numbers are first sorted and then and letters. In another embodiment the sorting will allow for the ordering BLA2, CD5 and CD12 as such. The tree sorts three agents and then it shows them either as a yellow folder (branch) or as a diamond (leaf). In another embodiment, application-specific icons are used to represent the branches and leaves. A plus (+) next to the yellow folder (or icon) indicates that it has information "in it" that can be displayed. Clicking the plus opens the folder and displays the information. A minus(−) indicates that the folder is open. Clicking it closes the folder.

In the embodiment shown, the tree is organized to show determinants at the first level, fluorescence colors of the fluorochrome-coupled reagents detecting the determinant at the second level, and preparation lots for each determinant at the third level. A fourth level may show the vials associated with each preparation lot. The tree may be organized differently, for example to show fluorescence colors at the top level and determinants at the second level.

Also, in the embodiment shown, CD5 2202 is open and has three determinants underneath it. If it were closed then there would be no visible determinants underneath. The diamonds specify which colors are available to use corresponding to detect the corresponding determinants. In the case of CD5, there are APC, Biotin and CasBlu. Since APC and CasBlu are not greyed out, i.e., are bright, they are available. Biotin is grayed. It is not available either due to a color conflict or to that reagent being out of stock.

Since CD25, B220, BLAII and BP-1 are highlighted in tree 2201 they appear in the protocol in the chart 2203. The user can deselect and select reagents automatically through the GUI either by clicking on the tree or the chart. Further, a user may click on a determinant and the system will then automatically take the user to an internal information page about the determinant or link the user, via an internet browser on the user's computer, to outside information sources such as NCBI or search engines. The chart 2203 is also constructed with information from the knowledge base.

Figure 22B:
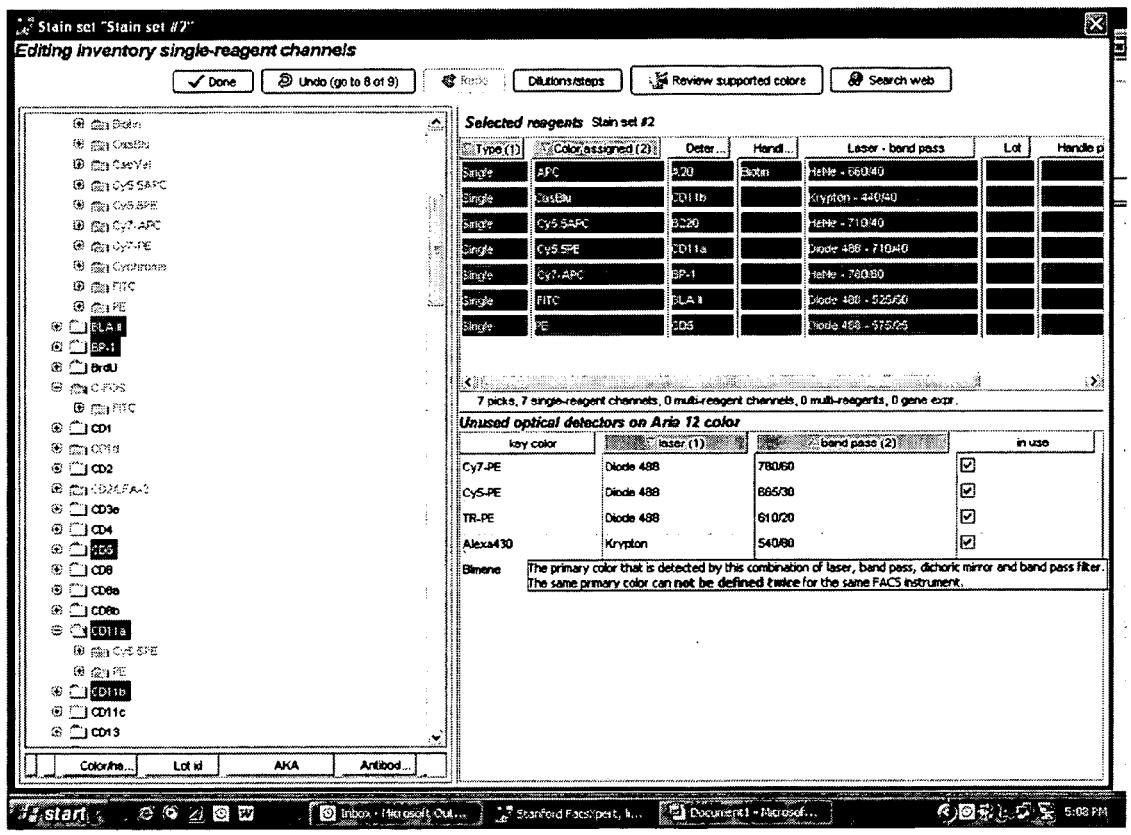

FIG. 22*b* shows a single reagent protocol with 7 select reagents. The reagents are selected in the tree and appear on the right side in a chart specifying information related to the protocol and the reagents. The user can select or deselect the reagents in many manners including by specifying the determinant, the color of the reagent or the lot of the reagent.

Figure 22C:
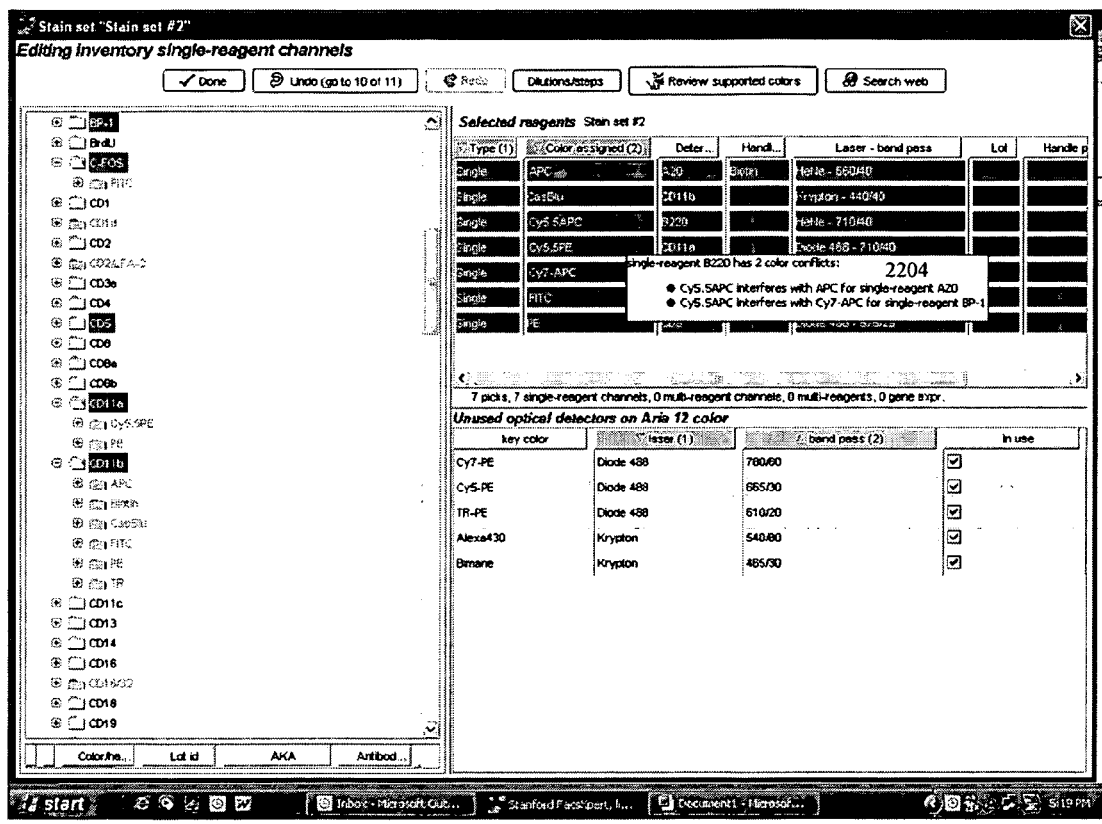

FIG. 22*c* show a box 2204 that allows a user to see the conflicts caused by adding a particular reagent to an experimental protocol. The conflict determination is performed by the system in conjunction with the knowledge base's information. Once a conflict is determined, the user may deselect the blocking reagent to allow the reagent that the user wishes to use to be added to the protocol. If the only available colors for a new reagent is already used in the protocol, the system can automatically reassign colors to accommodate the new reagent. As long as the reagent has not been greyed out by the system, the system can do the reassignments. This is accomplished by the system determining a feasible reagent cocktail with the reagent to be added and changing the reagents accordingly. When a feasible combination can no longer be found for a reagent, the system greys out the reagent on the tree. To include that reagent, the user must deselect some other reagent already included in the cocktail. Tool tips accessed by hovering over the greyed out determinant name in the tree advise the user as to which included reagent is causing the conflict.

Sometimes, the fluorescence colors have to be organized to prevent interference with detection of a weakly detected determinant. If a user selects a determinant in the tree structure, the reagents that can be influenced by spillover from other reagents will be highlighted in a red box in the reagent chart. This informs the user about which reagents should be removed in order to best detect a given determinant. In addition, the system can be set to automatically minimize interference between the reagents based on the interference data in the knowledge base. In other words, the interference between reagents is one of the possible inputs to the system when it is facilitating selection of a feasible and optimally functional reagent cocktail.

Figure 23:
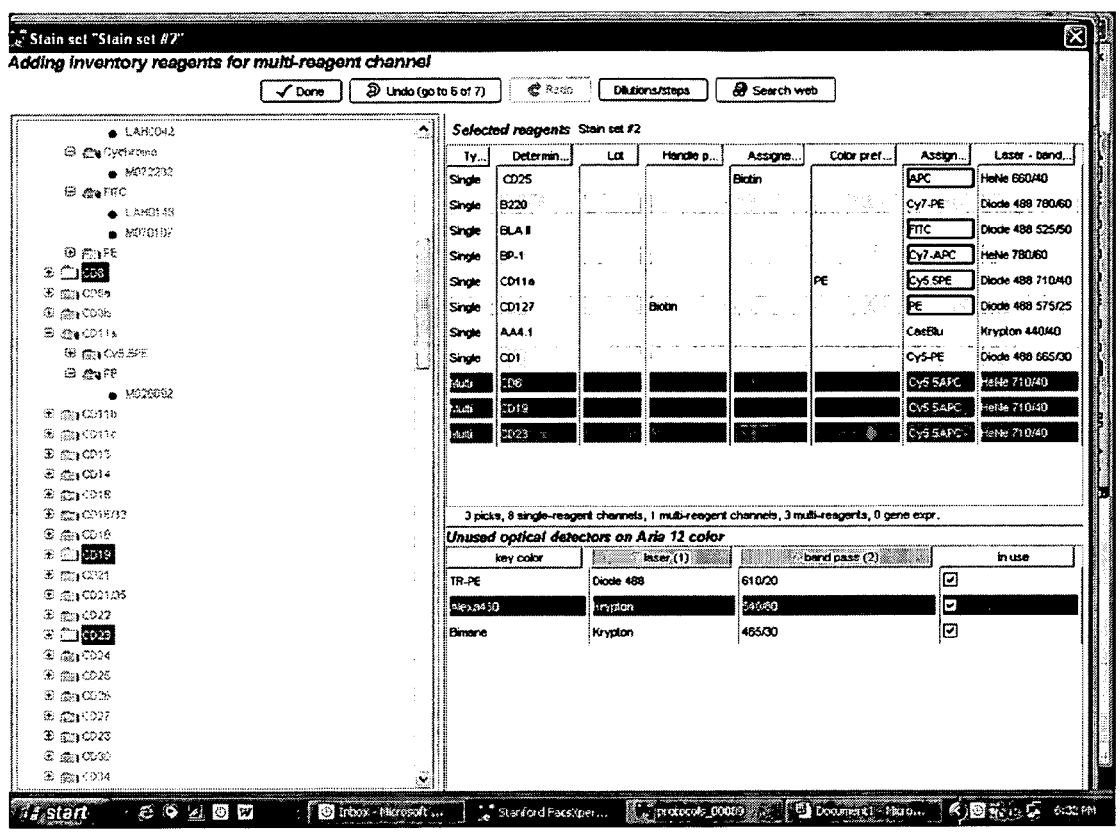

The chart in the bottom right reports on the optical detectors for the protocol. The chart on the right also includes the lot number, other technical details, and assigned color. It also provides a place for a user to interactively insert a preferred color. The system in one mode prevents reagents with overlapping/interfering colors from being selected. In a second mode it allows reagents with overlapping/interfering colors to be selected. This allows selection of reagents coupled to the same or similar fluorochromes, in order to detect multiple determinants with a single fluorescence detector. FIG. 23 shows a screen for adding determinants to such a multi-reagents channel protocol (a similar screen is available for a single-reagent channel protocol). In this example, CD8, CD19, and CD 23 are added to the protocol by clicking on them in the tree. They then appear highlighted in the chart on the right.

Figure 24:
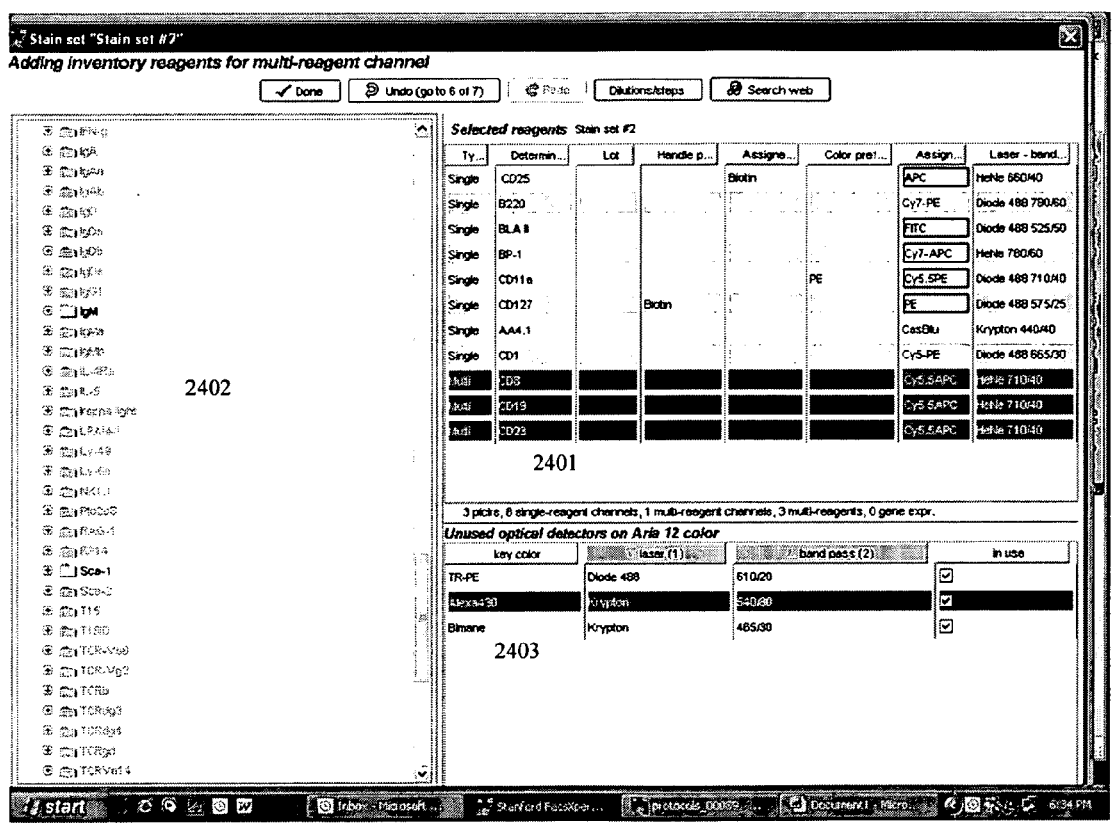
Figure 25:
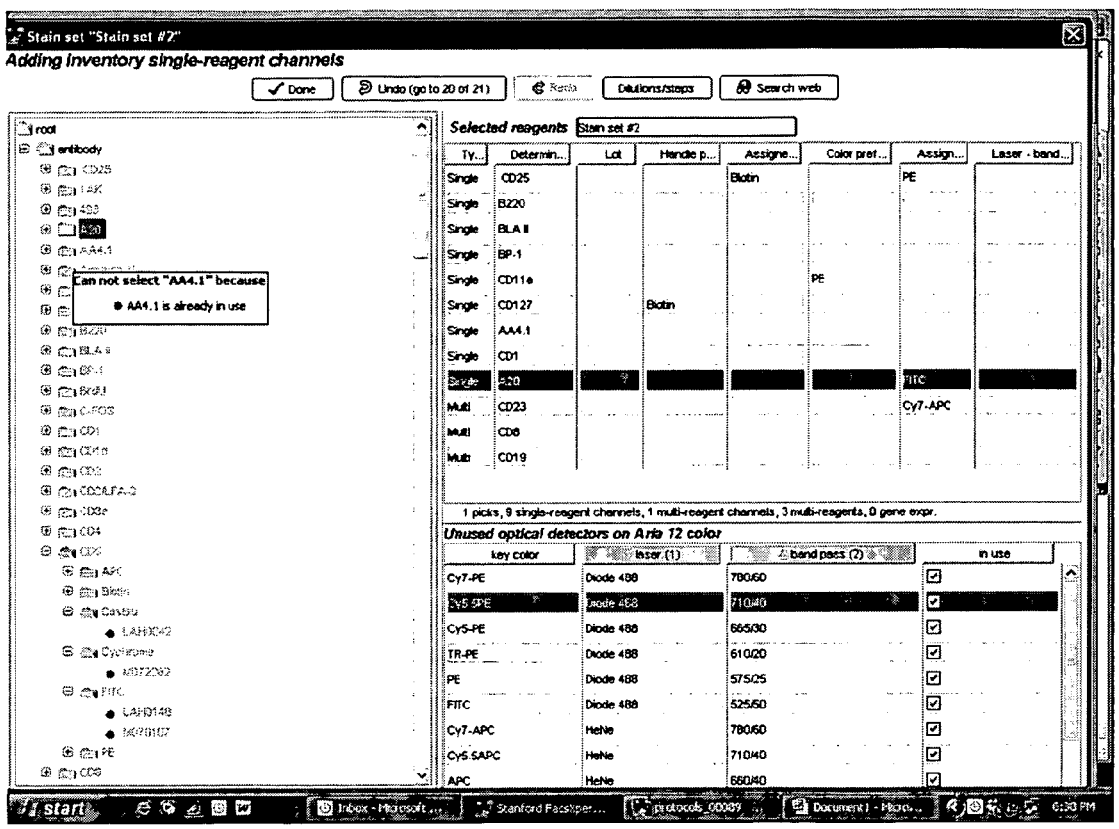

FIG. 24 shows the protocol after several reagents have been selected. Specifically, in chart 2401, 11 reagents have already been selected. Thus very few reagents can still be feasibly added to the protocol. This can be seen from the tree on the left 2402 where only IgM and Sca-1 can still be feasibly added to the protocol. The other grayed out reagents are not feasible within the protocol, even with changing the automatically selected colors. The chart 2403 shows the detectors that are still unused and available for addition into the protocol being created. In this case there are three unused detectors and the IgM or Sca-1 will either use that detector or take the detector of a reagent that can be implemented with one of those detectors. FIG. 25 shows a message to a user showing that a particular reagent cannot be used with the current protocol since including it in the reagent cocktail yields an infeasible protocol.

Figure 26A:
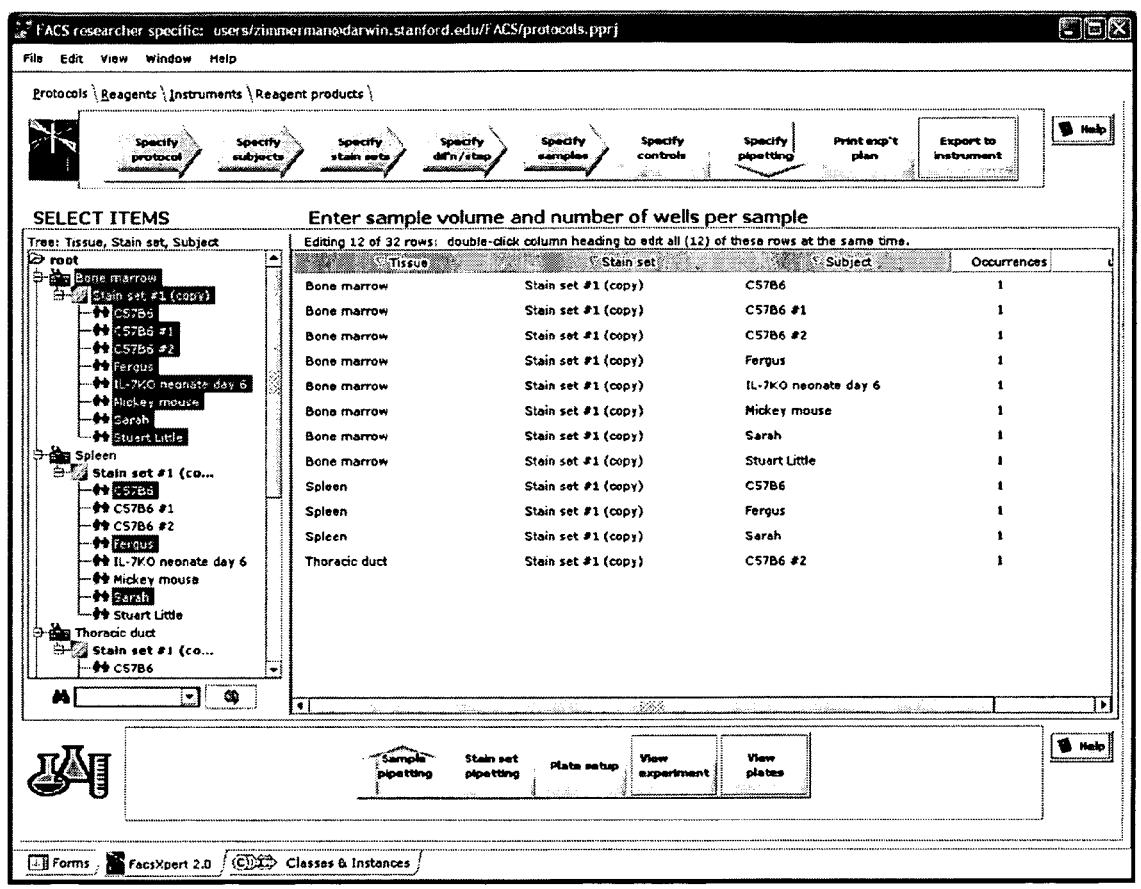
Figure 26B:
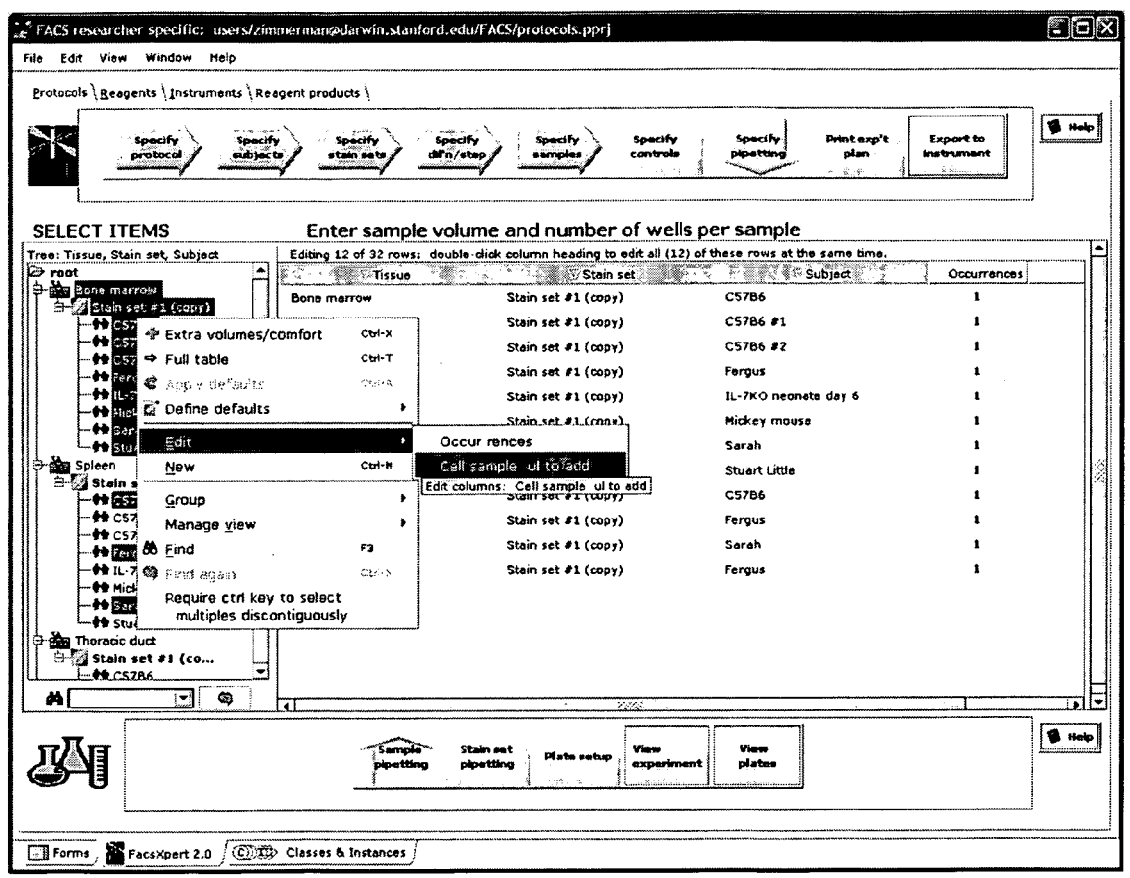
Figure 26C:
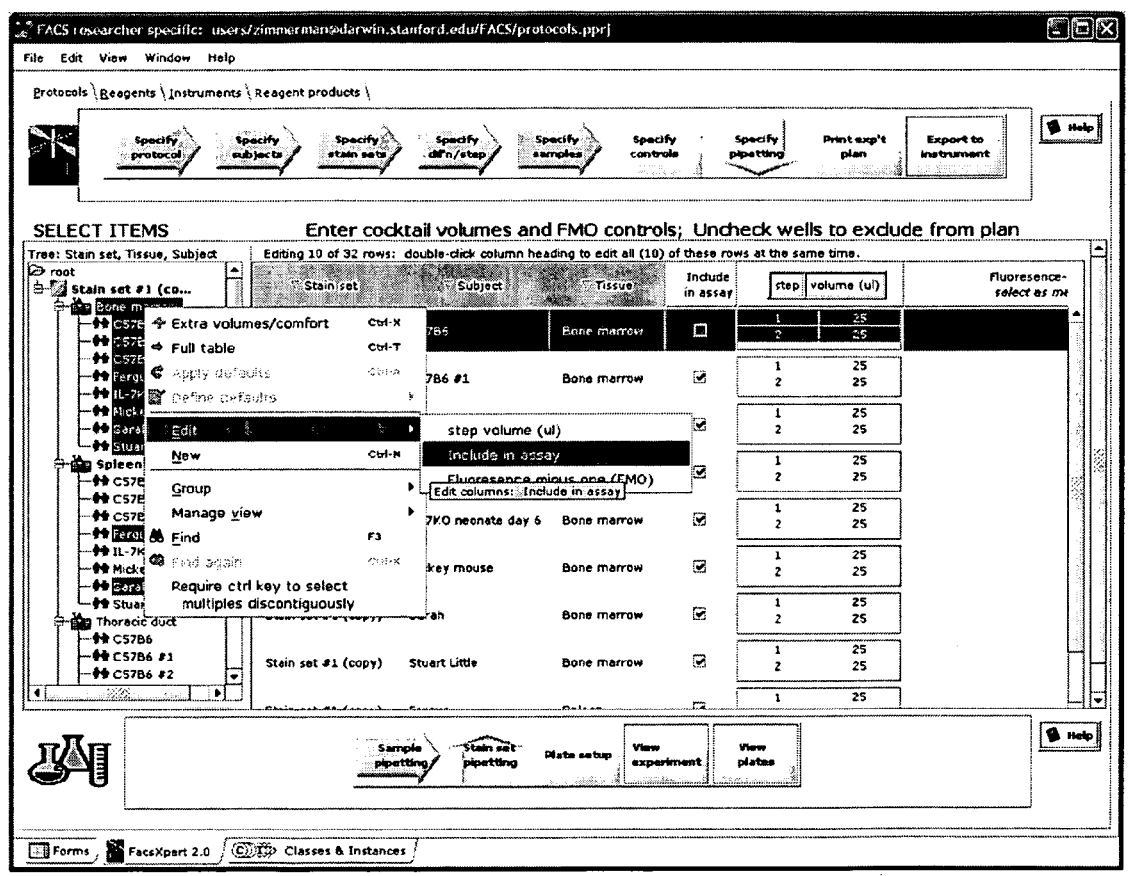
Figure 26D:
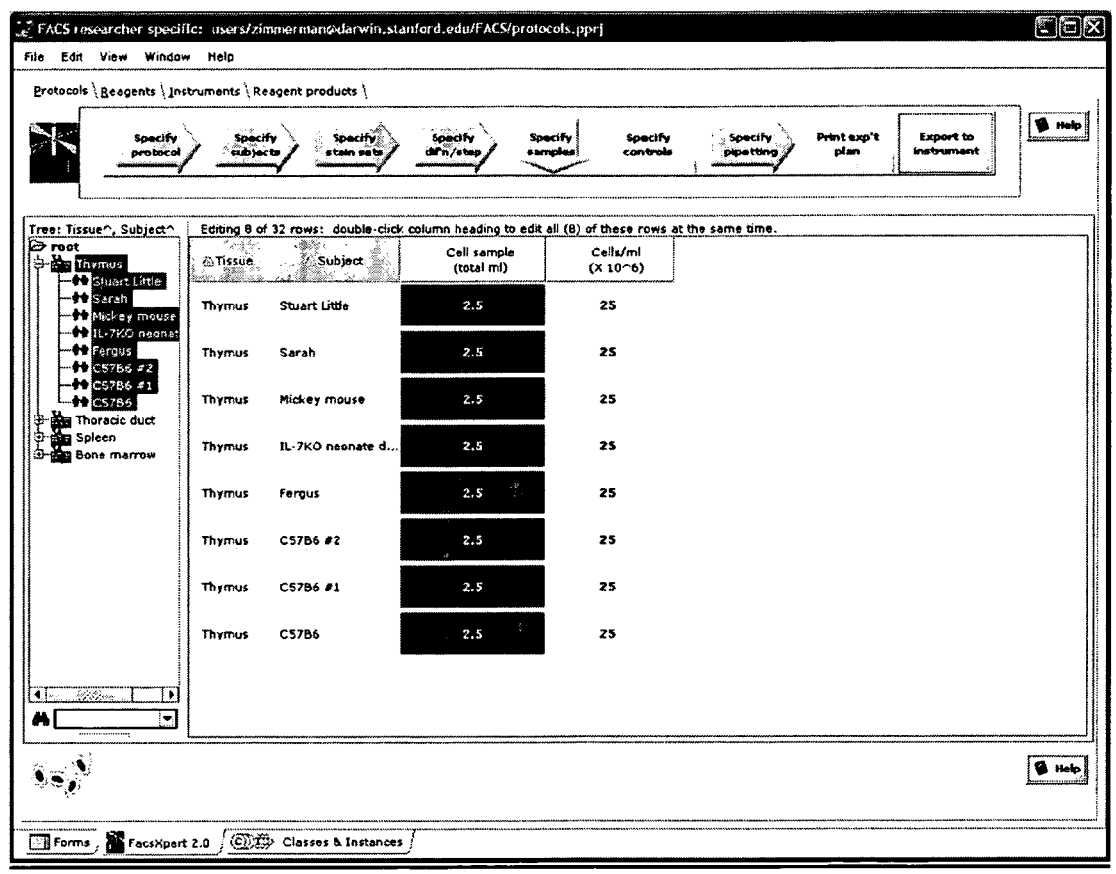

FIG. 26*a* shows a plate or test tube plan with which the user indicates which reagent cocktails are to be combined with which cell samples, specified as the cell types obtained from the subjects and identified both by subject name and cell type name. Many cell samples may be included in a single experiment. Some may be stained with all reagent cocktails; others may be stained only with a subsets of the cocktails that have been created. The system manages the combinatories which specifies the full experiment based on the samples and cocktails the user wished to combine. In addition, the system adds the relevant controls consistent with the general instruction about controls that the user provided earlier in the experiment set up.

To facilitate specification of which cell samples from which subjects are to be combined with which cocktails, and to facilitate entry of information about the contents of the samples, the system provides a flexible tree structure that enables group and individual access to samples. The system enables the user to order this tree structure and provides preset views of the tree structure. This tree structure, and its underlying table, is generalizable to computer representations of sets of items that can be organized hierarchically and for which selective group access is desirable.

The embodiment in FIG. 26*a-d* variously organized tree structures in the left panel and associated charts in the right panel. Buttons at the top indicate activities, e.g., specification of sample properties or specification of how the sample is to be pipetted. When a button is pressed, a preset tree structure appears on the left panel. The columns that appear on the right are preset to show the outcomes of the desired activity, e.g., how many milliliters of sample should be used for the test.

The user selects the group of samples for which the activity is to be indicates. Selecting at the lowest level of the tree selects individual items selecting at higher tree levels selects everything below the selected item. A higher level item can be selected and items below it can be individually de-selected. The table shows information only for those items that are selected. In some modes it shows one row for each selected item. In other modes, it shows one row for each group of items selected. These modes and the tree order are all specifiable by the user.

Right-click menus allow the user to perform actions such as entering values into columns, deleting values or changing values. The action will be performed for all items selected on the tree. Individual table cells or individual columns can also be edited directly. Choice of experiment controls such as the FMO control can be specified through this mechanism.

After all specifications of amounts and combinations are complete, a button at the top of the form allows the user to see the final results of the choices laid out as a "tube or plate" array showing the contents of each tube, including the volumes of cells and cocktails to be added. If the user is not satisfied with the choices listed, he/she can return to the previous screen to make adjustments.

Once satisfied with the tube/plate array contents, the user can request a summary of the experiment. The system then calculates and displays the amounts of all samples and reagents to be used and how they are to be combined. This display can be visualized with a browser or printed as charts to be used at the experiment bench.

Internet Database

The database may also be constructed using standard database techniques including the use of LDAP directories and protocols, XSLT style sheets, and XML documents. The database may be at a centralized site remote to the experimenter. The experimenter sends or receives information between his computer and the database via the Internet or any other communication means. LDAP is a "lightweight" (smaller amount of code) version of DAP (Directory Access Protocol), which is part of X.500, a standard for directory services in a network. The present invention puts these to unique uses in the scientific arena. In essence, the style-sheet transformation language (XSLT) defines the transformation of the original input (XML) document to "formatting objects" such as those included in HTML documents. In a traditional style sheet, these are then rendered for viewing. However, the XSLT transformation grammar can also be used to transform XML documents from one form to another, as in the following examples:

a) Loading directories. XSLT is used to transform an XML file generated by any data processing application to an XML representation of a directory (sub)tree, i.e., to extracting directories entries from the XML document. The ability to use XSLT for this transformation greatly simplifies the creation and maintenance of LDAP or other directories that serve diverse information derived from distinct sources (e.g, FACS instruments and genome data banks) that generate different types of XML documents. In essence, using XSLT removes the necessity for writing distinct Java code to construct the directory entries for each type of document. Instead, appropriate "directory styles" can be defined for each document type and a single Java program can be written to process all XSL-transformed documents into the directory tree.

b) Re-indexing directory entries. Existing documents may be readily re-indexed based on any desired elements or attributes present in the XML documents simply by changing the XSLT style sheet. Changes in the directory schema may be required for extensive indexing changes but could also be driven by an XML representation of the appropriate schema.

c) Cataloging new documents. A new type of document can be cataloged simply by creating an appropriate XSLT style sheet and modifying the directory schema if necessary, as above.

d) Cataloging from arbitrary XML documents. A default XSLT directory style sheet can be created to extract a pre-defined set of indexing elements included in arbitrary XML documents. This would enable creation of the corresponding directory entries for these indexing elements.

e) Passing information from XML files to analytic or other programs: XSLT can be used to transform a subset of the information in an XML file so that it can be read by a program that takes XML input in a particular format. In addition, XSLT can launch the program and pass the result of the transformation during the launch. For example, using XSLT stylesheets, we can launch an analysis application by transforming an XML file including the results of a directory search to an application-readable file including URLs for the data and appropriate annotation information for the analysis. This option can be made available for all co-operating applications and are not restricted to FACS data.

f) Creating data displays. XSLT style sheets can be used to change the form of a document. For example, they can be used to extract the results of analyses and display them as values in the rows or columns of a table.

As indicated above, XSLT and other capabilities may be used to store analysis output along with the primary data and annotation information. Alternatively, other developed fully cooperating applications may be used to analyze of FACS and other data.

A major advantage of LDAP is the availability of LDAP servers and client toolkits. Standalone servers and LDAP to X.500 gateways are available from several sources. LDAP client libraries are available for the C language from Univ. Michigan and Netscape and for the Java language from Sun and Netscape.

Secondly, LDAP is a standard that is directly utilized by the clients and makes it possible for all clients to talk to all servers. In contrast, SQL standardization may be more apt with transportability of programmers and database schema than interoperability of databases.

The X.500 information model is extremely flexible and its search filters provide a powerful mechanism for selecting entries, at least as powerful as SQL and probably more powerful than typical OODB. The standard defines an extensibleObject that can have any attribute. Furthermore, some stand-alone LDAP implementations permit relaxed schema checking, which in effect makes any object extensible. Since an attribute value may be a distinguished name, directory entries can make arbitrary references to one another, i.e., across branches of the directory hierarchy or between directories.

Finally, some LDAP and X.500 servers permit fine grained access control. That is to say, access controls can be placed on individual entries, whole sub trees (including the directory itself) and even individual attributes if necessary. This level of control is not available in most existing databases.

One example of an LDAP directory is organized in a simple "tree" hierarchy consisting of the following levels:

1) The "root" directory (the starting place or the source of the tree), which branches out to 2) Countries, each of which branches out to 3) Organizations, which branch out to 4) Organizational units (divisions, departments, and so forth), which branches out to (includes an entry for)

5) Individuals (which includes people, files, and shared resources such as printers)

Figure 2:
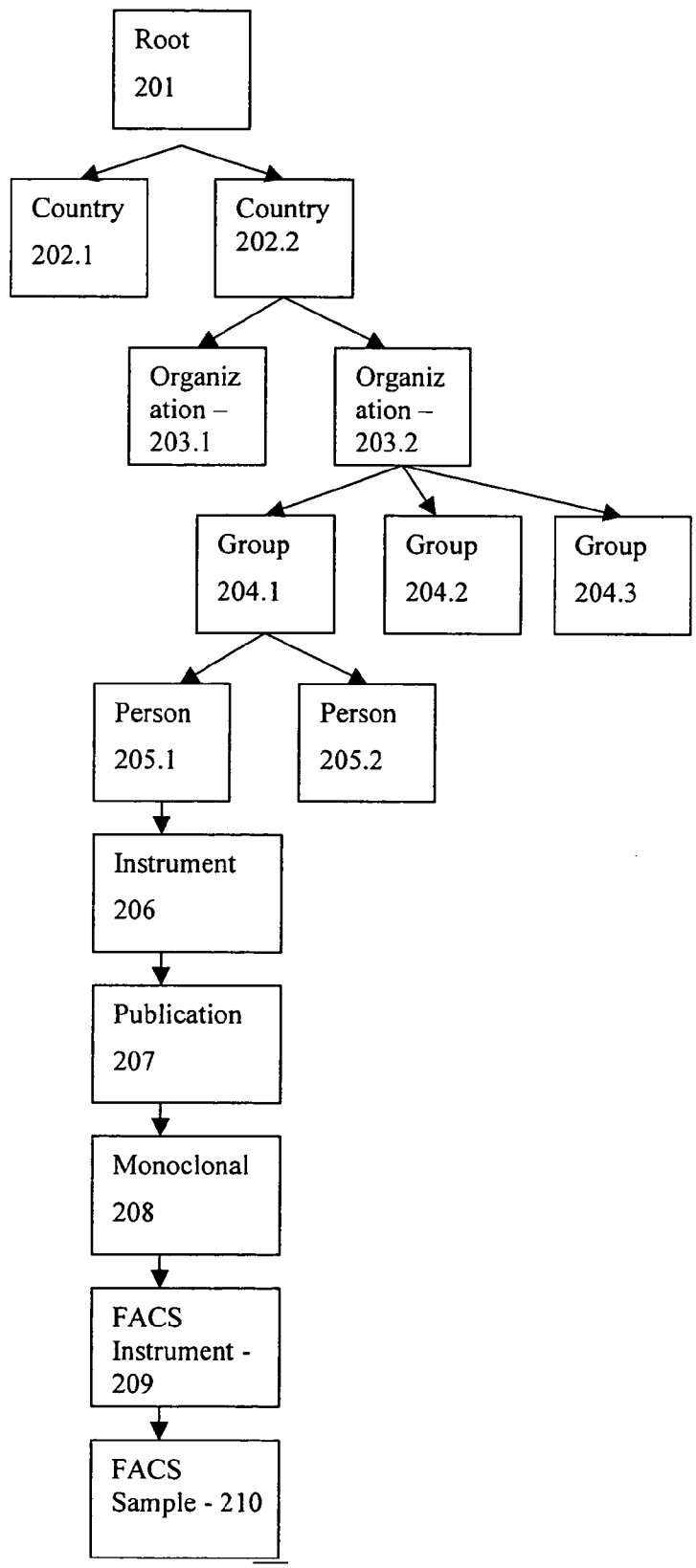
FIG. 2 is a diagram of a directory archival system

This example tree structure of an LDAP directory is illustrated in FIG. 2. The parent node of the tree is the root node 201. The children of the root directory are country nodes 202.1 and 202.2. Each country node can have child organization nodes such as organization nodes 203.1 and 203.2 (children of country node 202.2).

Below the organization level are organization group nodes such as nodes and 204.3 which are children of organization node 203.2 Each group can have children nodes representing individuals such as group node 204.3 having children nodes 205.1, 205.2, and 205.3.

In a network, a directory tells you where in the network something is located. On TCP/IP networks (including the Internet), the Domain Name System (DNS) is the directory system used to relate the domain name to a specific network address (a unique location on the network). However, sometimes the domain name is not known. There, LDAP makes it possible to search for an individual without knowing the domain.

An LDAP directory can be distributed among many servers. Each server can have a replicated version of the total directory that is synchronized periodically. An LDAP server is called a Directory System Agent (DSA). An LDAP server that receives a request from a user takes responsibility for the request, passing it to other DSAs as necessary, but ensuring a single coordinated response for the user.

The present invention contemplates extensions and modifications to LDAP protocols to make them usable not just as directories, but to also provide data itself. The present invention takes advantage of hierarchical levels of LDAP already established by the International Standards Organization (ISO) and uses those organizations to provide a first level of uniqueness to the biological sample to be named.

Referrals mean that one server which cannot resolve a request may refer the user to another server or servers that are capable of doing so. During a search operation any referrals encountered are returned with the entries located and the user (or client) has the option of continuing the search on the servers indicated. This allows federation of directories which means that multiple LDAP/X.500 servers can present to the user a unified namespace and search results even though they are at widely separated locations and the implementations may actually be very different.

The Java Naming and Directory Interface (JNDI) is a standard extension to the Java language introduced Java Naming and Directory Interface by Sun. It includes an abstract implementation of name construction and parsing that encompasses the X.500 name space (among others), and an abstract directory that is essentially the X.500 information and functional models. Specific implementations (service providers[13]) are available for LDAP, Network Information Server (NIS) and even the computers own file system.

JNDI may remove many of the limitations of LDAP as an OODB by providing a standard way to identify the Java class corresponding to a directory entity and instantiate it at runtime. It also allows storage of serialized Java objects as attribute values. Sun has proposed a set of standard attributes and objectClasses to do this.

When represented as a string (essentially always with LDAP) an X.500 distinguished name is a comma separated list of attribute value pairs and is read from right to left. If a value includes special characters such as commas it must be quoted and in any case initial and final white space around attributes or values is ignored. For example, "cn=Wayne Moore, ou=Genetics Department, o=Stanford University".

Location names may have as their root (right most) component the countryName or c attribute with the value being one of the ISO standard two letter country codes, for example c=US. Such names can be further restricted by specifying a stateOrProvinceName abbreviated st and a locality abbreviated l, for example "l=San Francisco, st=California, c=US".

Organizational names may have as their root the name (registered with ISO) of a recognized organization and may be further qualified with one or more organizational units, for example "ou=Department of Genetics, ou=School of Medicine, o=Stanford University".

Domain names as used by the Domain Name Service (DNS) are represented with the dc attribute, for example, "dc=Darwin, dc=Stanford, dc=EDU".

Names of persons. There are two conventions for naming people. The older uses the commonName or cn attribute of the Person objectClass but these are not necessarily unique. Some directories use the usernd or UID attribute of inetOrgPerson, which is unique. Since uniqueness is important for scientific applications the latter may be used. The remainder of a person's dn is usually either an organizational or geographic name, for example "uid=wmoore, o=Stanford University" or "cn=Wayne Moore, l=San Francisco, st=California, c=US".

Examples of encapsulating and extending existing nomenclatures:

1. Gene loci, for example, "locus=Igh-1, o=Professional Society or locus=New, cn=Leonard Herzenberg, ou=Department of Genetics, ou=School of Medicine, o=Stanford University".
2. Gene alleles, for example, "allele=a, locus=Igh-1, o=Professional Society or allele=1, locus=127, ou=Department of Genetics, o=Stanford University".
3. CD antigens, for example, "specificity=CD23, o=Human Leukocyte Differentiation Workshop".
4. Literature references in the scientific literature are essentially achieved the benefits of distinguished names without an explicit central authority. However representing them as distinguished names may facilitate mechanical processing. For example, "title="A Directory of Biological Materials", volume=1999, o="Pacific Symposium on Biocomputing". A true directory of such literature references would be of great value over and above the current unique naming systems in some of the current literature archives.
5. New nomenclature schema. The following schemas arose from work on storing information about flow cytometry data in directories.
6. Monoclonal antibodies are distinguished by cloneName or clone which is unique within the parent entity which must be an investigator or organization.
7. Lymphocyte differentiation antigens, a thesaurus of the target specificities of monoclonal antibodies. Would include but not be limited to the official CD names.
8. FACS instruments are distinguished by the cytometer attribute which must be unique with respect to the organization parent, for example, "cytometer=Flasher II, ou=Shared FACS Facility, o=Stanford University".
9. FACS experiments are distinguished by the protocolidentifier or protocol attribute which must be unique with respect to the parent which may be a person, and instrument or and organization or some combination, e.g., "protocol=1234, cytometer=Flasher, uid=Moore, ou=Shared FACS Facility, o=Stanford University".
10. FACS samples are distinguished by a unique protocol-Coordinate which must be unique within the parent FACS experiment, e.g., "coord=A12a, protocol=12345, cytometer=Mollusk, ou=Shared FACS Facility, o=Stanford University".

Therefore, using LDAP, any object, such as a monoclonal antibody, is advantageously namable relative to the unique distinguished name of an investigator or organization. That means that unique identifiers can be assigned to biological materials early in the scientific process and thus facilitate professional communication both informal and published. In the future, investigators who have this distinguished name can identify the material unambiguously via the unique name. If a directory services is maintained, an investigator can determine if the sample has been given an official name, if it has been shown to be equivalent to another entity or if it has been cited in the literature.

Directory searches are also a tool available in the database. Information may be promoted upward from the documents into the directory for searching and no searching is done within the documents. However, since XQL or Xpath allows searches to proceed downwards from the directory, a search application uses, for instance, the LDAP search functions to retrieve a set of candidate XML documents (based on their directory attributes) and then uses XQL or Xpath to further refine this set. To facilitate XQL or Xpath use, a unified interface may be provided that would largely make the differences in search strategies transparent to the user. The user then is then able to select (search and retrieve) for items within the document that are not reflected in the directory or may extract elements from these documents, e.g., samples from a set of experiments.

The instruments are capable of being responsible to collect, annotate and export the collected experimental data. These instruments annotate experimental data with information generated during the data collection, and for transmit the annotated primary data to the LDAP server for storage in the database in association with the appropriate XML-encoded experiment and study descriptions. As an example, the following modules may be used to perform these functions:
  a) Set-up module(s)—automate aspects of instrument set-up and standardization; record and visualize relevant instrument information; acquire and respond to user input
  b) Data collection module(s)—collect primary (instrument-generated) data for the aliquots of each sample; visualize protocol information to facilitate data collection; acquire and respond to user input; record machine condition and user comments specific to each data collection.
    i) adapt and interface the data collection modules to specific machines (e.g., various FACS, imaging and DNA-array data readers) to provide full functionality for data collection.
    ii) For instruments that do not provide/permit direct access to machine control and data collection, use additional modules that may enable manual entry of machine information and "point-and-click" association of primary data collected for each sample aliquot with the protocol information for that aliquot.
  c) Extension of the FACS document type—include new functionality such as instrument setup, auto-calibrator and quality control elements, tabulated transfer functions and operator commentary in the definitions of the FACS document type. Provisions for digests of the data files that are referenced and for digital signatures may also be made.
  d) Data transmission module(s)—link (annotate) the primary data with protocol instrument-derived information; communicate authenticated (digitally-signed) primary data and its annotation linkages to the information store.

The central database may be a large scale (terabyte level), web accessible, central storage system coupled with small-scale volatile storage deployed locally in a manner transparent to the user. This system stores data and annotation information transmitted from the data collection system. In addition, it catalogs the stored data according to selected elements of the structured annotation information and retains all catalog and annotation information in a searchable format. Wherever possible, industry standard formats for storing data and annotation information will be implemented. If no standard is available, interim formats may be used and may allow for translators to industry standards once the industry standards become available.

The database capitalizes on the built-in replication and referral mechanisms that allow search and retrieval from federated LDAP networks in which information can be automatically replicated, distributed, updated and maintained at strategic locations throughout the Internet. Similarly, because pointers to raw data in LDAP are URLs to data store(s), the database capitalizes on the flexibility of this pointer system to enable both local and central data storage.

The database enables highly flexible, owner-specified "fine-grained" access controls that prevent unauthorized access to sensitive information, facilitate sharing of data among research groups without permitting access to sensitive information, and permit easy global access to non-sensitive data and analysis results.
  a) Built-in access controls that may prevent release of unauthorized information from the system
  b) Multi-level access controls that may allow data owners to specify which users, or classes of users, are permitted to retrieve individual data sets and/or to access individual elements of the annotation information during searches
  c) User identity verification system that may be referenced by the access control system
  d) Anonymous access to data and annotation information that owners may make available for this purpose
  e) Security and encryption may be implemented to protect the information in the database itself as well in the communications between the central data repository and the remote locations.

The central database also allows for the retrieval of annotated data sets (subject to owner-defined accessibility) via catalog browsing and/or structured searches of the catalog. The central database also automatically verifies authenticity of the data based on the data's digital signature. This function is accomplished in one embodiment by launching internal and co-operating data analysis and visualization programs and transfer the data and annotation information to the program. Further the database puts the data and annotation information into published-format files that can be imported into data analysis and visualization programs that do not provide launchable interfaces.

The central database also allows for retrieval of analysis output. This function is accomplished in one embodiment by recovering/importing the link analysis output with primary and annotation data to provide access to findings via subject and treatment information that was entered at the study and experiment levels. This allows the database to store and catalog output from co-operating analysis programs (within the limitations imposed by the capabilities of analysis programs that were not designed for this purpose). It also allows the database to use internal analytic modules and programs that enables users to fully capitalize on the annotation information entered into the system.

What is claimed is:

1. A laboratory data management and protocol creation system, used to create an experiment plan or protocol, including:
  (a) an ontology knowledge module embedded in a server architecture that enables controlled simultaneous access by multiple users, wherein the server architecture comprises a computer processor, configured to store characteristics and controlled references for at least one of laboratory reagents, experiment subjects, tissues and cells as data in the ontology knowledge module;
  (b) an experiment input module configured to accept input of at least one parameter of an experiment to be executed, wherein the at least one parameter of the experiment is selected from entries in the configured ontology knowledge module, and wherein the at least one parameter is annotated with data from the experiment input module; and
  (c) an automated protocol creator module connected to the ontology knowledge module and the experiment input module, wherein the automated protocol creator module is configured to create and annotate a laboratory protocol for an experiment that then is executed based on inputs from the ontology knowledge module and the experiment input module.

2. The system of claim 1, wherein the system is programmed in an object oriented language.

3. The system of claim 1, further including a laboratory inventory module configured to store an inventory of laboratory materials and connected to the protocol creator module, wherein the protocol creator module is further configured to take input information from the laboratory inventory module when creating the laboratory protocol.

4. The system of claim 1, further including at least one laboratory data storage module configured to store results from at least one laboratory experiment, the at least one laboratory data storage module connected to the protocol creator module.

5. The system of claim 4, wherein the protocol creator module is further configured to take input information from the laboratory data storage module when creating a laboratory protocol.

6. The system of claim 5, further including a laboratory experiment analysis module configured to analyze data of at least one experiment, wherein the laboratory experiment analysis module is connected to the laboratory data storage module and the protocol creator module.

7. The system of claim 6, wherein the laboratory experiment analysis modules is configured to perform cluster analysis on data of at least one experiment.

8. The system of claim 4, wherein the system is configured to store at least one of the experiment, protocol and data in the laboratory data storage module.

9. The system of claim 8, wherein the system is configured to store the at least one of the experiment, protocol and data to a unique file location that is named and controlled by the laboratory data storage module.

10. The system of claim 9, wherein the unique file location is accessible through a Uniform Resource Locator (URL) reference.

11. The system of claim 4, wherein the laboratory data management system includes a searchable directory of items in the data storage module.

12. The system of claim 11, wherein the searchable directory includes information from at least one of the experiment, an analysis and the laboratory protocol stored as searchable metadata.

13. The system of claim 12, wherein the directory is configured to provide data annotated with metadata to the laboratory experiment analysis module.

14. The system of claim 11, wherein the knowledge module is configured to search the searchable directory.

15. The system of claim 3, wherein the protocol creator module is configured to determine and output feasible combinations of materials used for the laboratory protocol.

16. The system of claim 15, wherein the materials include at least two Fluorescent Activated Cell Sorting (FACS) machines, FACS machine configurations, Microarray machines, Microarray machine configurations, reagents and chemicals.

17. The system of claim 4, wherein the data management system is configured to take input from a user and provide output to a user though a graphical user interface.

18. The system of claim 17, wherein the graphical user interface outputs an interactive diagram of a layout for the laboratory protocol.

19. The system of claim 18, wherein the layout is a laboratory experiment organizational matrix including at least one of a well plate, a test tube rack, Enzyme-Linked Immunosorbent Assay (ELISA) array, and Microarray.

20. The system of claim 17, wherein the user is capable of interactively changing the laboratory protocol by changing information within the layout presented by the laboratory protocol.

21. The system of claim 17, wherein the graphical user interface is configured to present the user a tree structure configured to enable selection of a group of nodes including any two nodes.

22. The system of claim 21, wherein the system is configured to permit a noncontiguous selection, wherein;
a first child node is deselected after a first parent node is selected; and
a second child node is deselected after a second parent node is selected;
wherein the first parent node is not a parent of the second parent node; and
the second parent node is not a parent of the first parent node.

23. The system of claim 22, wherein the system is configured to determine if an edit made by the user in the graphical user interface is valid for all the selected nodes.

24. The system of claim 20, wherein the graphical user interface is configured to automatically update the laboratory protocol in the protocol creator module when the laboratory protocol is altered by a user within the graphical user interface.

25. The system of claim 17, wherein the graphical user interface is configured to automatically update the knowledge module when the knowledge base is altered by a user within the graphical user interface.

26. The system of claim 1, wherein the knowledge module is configured to be updated through a data import export Application Program Interface (API).

27. The system of claim 1, wherein the knowledge module is configured to be updated by an updating module, the updating module is connected to the knowledge module and the data storage module and reviews experimental data to determine if the knowledge module should be updated and upon such determination updates the knowledge module.

28. The system of claim 4, further including a scheduling module connected to the protocol creator module, wherein the schedule module is configured to schedule use times for experiments based on availability of usable laboratory instruments including at least one of a FACS machine and a Microarray reader.

29. The system of claim 4, further including a scheduling module connected to the protocol creator module and knowledge module module, wherein the scheduling module is configured to determine appropriate laboratory instruments to be used for experiments based on the characteristics and capabilities of the laboratory instruments including FACS machines and Microarray reader.

30. The system of claim 28, wherein an instrument control module connected to the knowledge module and the protocol creator module is configured to:
import information from the knowledge module and protocol creator module; and
export information, based on the imported information, to a laboratory instrument selected for a protocol, wherein the exported information is used to at least one of the following: set up the instrument, standardize the instrument, set instrument parameters, name data files for the instrument output corresponding to the laboratory protocol, label instrument display parameters, and drive data collection based on the laboratory protocol.

31. The system of claim 17, wherein the graphical user interface is configured to allow users to search metadata to determine which past experiments stored in the at least one laboratory data storage module match a query by the user.

32. The system of claim 18, wherein the protocol creator module is configured to implement combinatories algorithms to determine feasible products.

33. The system of claim 32, wherein a check-in module is configured to receive information from at least one of the protocol maker module, an instrument, the knowledge module and the user and couples the information to data files connected to an experiment and is further configured to package and store the data files in the data storage module.

34. The system of claim 12, wherein the search is based on the input of a combination of metadata.

35. The system of claim 34, wherein the search module is configured to output a graphical user interface to a user to allow the user to retrieve results of a search; and wherein the system further includes a hypothesis testing module connected to the system configured to test an inputted hypotheses based on inputted data and to output the result of a hypothesis test through the graphical user interface.

36. A method for creating a laboratory protocol to be used in conducting an experiment, the method including the steps of:
   (a) storing characteristics and controlled references for at least one of laboratory reagents, experiment subjects, tissues and cells in an ontology knowledge module embedded in a server architecture that enables controlled simultaneous access by multiple users, wherein the server architecture comprises a computer processor, as data in the ontology knowledge module;
   (b) accepting input through an experiment input module of at least one parameter of the experiment to be executed, wherein the at least one parameter of the experiment is selected from entries in the configured ontology knowledge module, and is annotated with data from the experiment input module; and
   (c) automatically creating and annotating a laboratory protocol by an automatic protocol creator module for the experiment based on inputs from the ontology knowledge module and the experiment input modules.

37. The method of claim 36, wherein portions of the ontology knowledge module is written in an object oriented language.

38. The method of claim 36, further including the steps of storing an inventory of laboratory materials in a laboratory inventory module connected to the protocol creator module, and receiving input information from the laboratory inventory module when creating the laboratory protocol.

39. The method of claim 36, further including the step of storing results from at least one laboratory experiment in at least one laboratory data storage module, the at least one laboratory data storage module connected to the protocol creator module.

40. The method of claim 39, further including the step of taking input information by the protocol creator module from the laboratory data storage module when creating the laboratory protocol.

41. The method of claim 40, further including the step of analyzing a laboratory experiment by an experiment analysis module of at least one experiment, wherein the laboratory experiment analysis module analyzes data from the laboratory data storage module and the protocol creator module.

42. The method of claim 41, further including the step of performing cluster analysis on data of at least one experiment by the experiment analysis module.

43. The method of claim 39, further including the step of storing at least one of the experiment, protocol and data in the laboratory data storage module.

44. The method of claim 43, further including the step of storing the at least one of the experiment, protocol and data to a unique file location that is named and controlled by the laboratory data storage module.

45. The method of claim 44, wherein the unique file location is accessible through a URL reference.

46. The method of claim 39, further including the step of searching a directory of items in the data storage module.

47. The method of claim 46, wherein the directory includes information from at least one of an experiment, an analysis and the laboratory protocol stored as searchable metadata.

48. The method of claim 47, further including the step of providing data annotated with metadata to the laboratory experiment analysis module.

49. The method of claim 46, further including the step of searching by the knowledge module of the searchable directory.

50. The method of claim 38, further including the steps of determine and outputting by the protocol creator module feasible combinations of materials used for the laboratory protocol.

51. The method of claim 49, wherein the materials include at least two of FACS machines, FACS machine configurations, Microarray machines, Microarray machine configurations, reagents and chemicals.

52. The method of claim 39, further including the step of taking input from a user by the protocol maker module and providing output of a laboratory protocol to a user through a graphical user interface.

53. The method of claim 52, further including the step of outputting an interactive diagram of a graphical user interface layout for the laboratory protocol.

54. The method of claim 53, wherein the layout is a laboratory experiment organizational matrix including at least one of a well plate, a test tube rack, enzyme-linked immunosorbent array and microarray.

55. The method of claim 49, including the step of changing the laboratory protocol by the user by changing information within the layout presented by the laboratory protocol.

56. The method of claim 49, including the steps of presenting to a user the graphical tree structure, and selecting of a group of modes including any two nodes.

57. The method of claim 56, including the step of selecting a noncontiguous selection of a group of nodes, wherein:
   a first child node is deselected after a first parent node is selected; and
   a second child node is deselected after a second parent node is selected;
wherein the first parent node is not a parent of the second parent node; and
   the second parent node is not a parent of the first parent node.

58. The method of claim 57, including the step of determining if an edit made by the user in the graphical user interface is valid for all the selected nodes.

59. The method of claim 55, including the step of updating by the graphical user interface the protocol in the protocol creator module when the protocol is altered by a user within the graphical user interface.

60. The method of claim 52, including the step of updating the knowledge module when the knowledge module is altered by a user within the graphical user interface.

61. The method of claim 36, including the step of updating the knowledge module through a data import export application program interface.

62. The method of claim 36, including the steps of:
receiving information by the updating module from the ontology knowledge module and the data storage modules;
reviewing experimental data by the updating module to determine if the knowledge module should be updated; and
updating the knowledge module.

63. The method of claim 39, including the step of scheduling use times for experiments based on availability of usable laboratory instruments including at least one of FACS machines and microarray reader.

64. The method of claim 39, further including determining appropriate laboratory instruments to be used for experiments based on the characteristics and capabilities of the laboratory instruments including at least one of a FACS machine and a microarray reader.

65. The method of claim 63, further including the steps of:
importing information by an instrument control module from the knowledge module and protocol creator module; and
exporting information, based on the imported information, to a laboratory instrument selected for a protocol, wherein the exported information is used to at least one of the following: set up the instrument, standardize the instrument, set the instrument parameters, name data files for the instrument output corresponding to the protocol, label instrument display parameters, and drive data collection based on the protocol.

66. The method of claim 62, including the step of searching metadata to determine which past experiments stored in the at least one laboratory data storage module match a query by the user on a graphical user interface.

67. The method of claim 36, further including the step of configuring the protocol creator module to implement combinatories algorithms to determine feasible protocols.

68. The method of claim 67, including the steps of:
receiving by checking module information from at least one of the protocol maker module, an instrument, the ontology knowledge module and the user;
coupling the information by the checking module to data files connected to an experiment; and
packaging and storing the data files in the data storage module.

* * * * *